US006548017B2

(12) United States Patent
Krivitski et al.

(10) Patent No.: US 6,548,017 B2
(45) Date of Patent: *Apr. 15, 2003

(54) METHOD FOR REAL TIME MONITORING OF BLOOD VOLUME IN A FILTER

(75) Inventors: Nikolai M. Krivitski, Ithaca, NY (US); Victor V. Kislukhin, Moscow (RU)

(73) Assignee: Transonic Systems, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/337,109

(22) Filed: Jun. 21, 1999

(65) Prior Publication Data

US 2002/0009385 A1 Jan. 24, 2002

Related U.S. Application Data

(63) Continuation of application No. 09/047,016, filed on Mar. 24, 1998, now Pat. No. 5,928,128.
(60) Provisional application No. 60/041,691, filed on Mar. 25, 1997.

(51) Int. Cl.[7] .................. A61M 1/36; A61M 37/00; B01D 11/00
(52) U.S. Cl. .................. 422/44; 604/5.01; 210/646; 210/85; 73/861
(58) Field of Search ................ 604/4.01, 5.01, 604/6.09; 600/300, 314, 322, 366, 454, 456, 459–68, 504–5; 128/898; 210/646, 647, 85; 73/61.63, 61.43, 61.64, 861, 196, 861.04, 861.05

(56) References Cited

U.S. PATENT DOCUMENTS 3,838,774 A    10/1974   Dolan et al.
RE30,007 E      5/1979   Steuer et al.
4,937,557 A     6/1990   Tucci et al.
4,995,268 A     2/1991   Ash et al.
5,230,341 A  *  7/1993   Polaschegg ............ 128/668
5,351,686 A    10/1994   Steuer et al.
5,372,136 A    12/1994   Steuer et al.
5,403,497 A     4/1995   Schultz et al.
5,409,612 A     4/1995   Maltais et al.
5,453,576 A  *  9/1995   Krivitski
5,486,286 A     1/1996   Peterson et al.
5,567,320 A    10/1996   Groux et al.
5,576,493 A    11/1996   Jowinski
5,644,240 A     7/1997   Brugger
5,676,824 A    10/1997   Jeon et al.
5,744,027 A     4/1998   Connell et al.
5,779,911 A     7/1998   Haug et al.
5,792,367 A     8/1998   Mattisson et al.
5,803,908 A     9/1998   Steuer et al.
5,928,180 A  *  7/1999   Krivitski et al. .......... 604/4
5,980,465 A  * 11/1999   Elgas .................... 600/504
6,117,099 A  *  9/2000   Steuer et al.

* cited by examiner

*Primary Examiner*—Angela D. Sykes
*Assistant Examiner*—Patricia Bianco
(74) *Attorney, Agent, or Firm*—Brian B. Shaw, Esq.; Stephen B. Salai, Esq.; Harter, Secrest & Emery LLP

(57) ABSTRACT

A method and apparatus for monitoring and measuring the filter blood volume by dilution techniques in real time, wherein the filter may be in use or off line during the measurements. The system includes a method and apparatus for measuring or monitoring the volume of a blood side of a filter by employing one of a bolus in the blood side upstream of the filter; a change of the filtration rate in the filter; and a bolus on the dialysate side, wherein the filter blood volume is calculated from the obtained data.

7 Claims, 14 Drawing Sheets

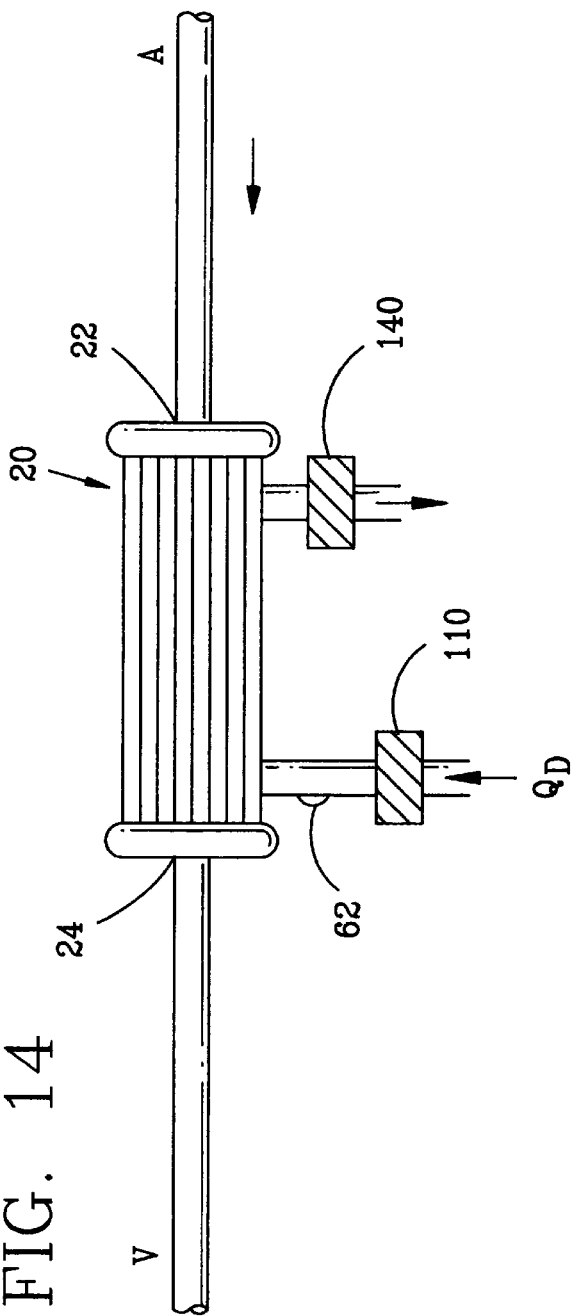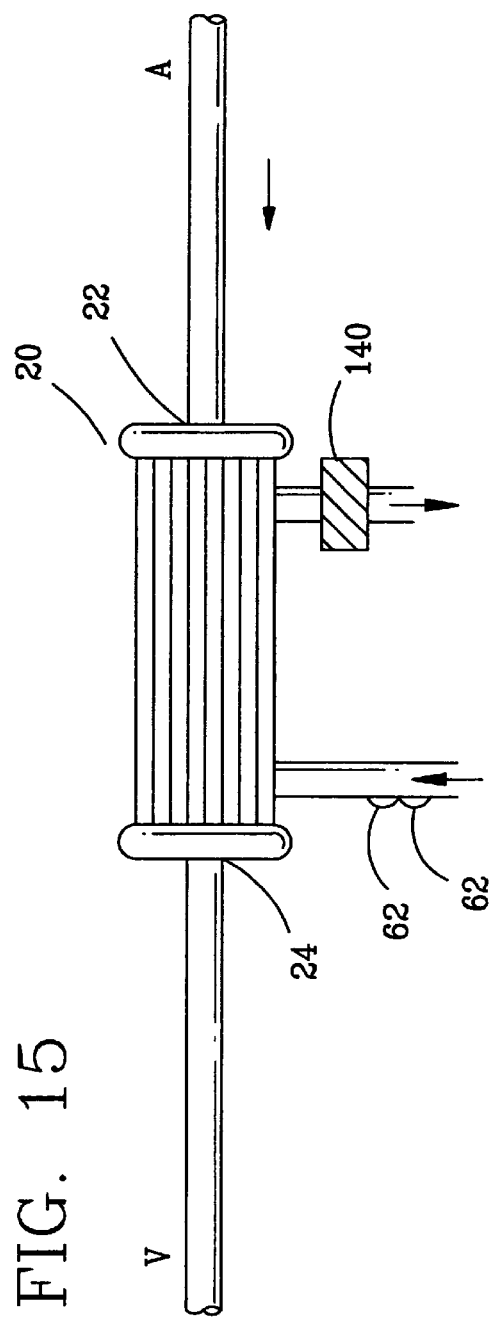

METHOD FOR REAL TIME MONITORING OF BLOOD VOLUME IN A FILTER

This application is a continuation of U.S. Ser. No. 09/047,016; filed Mar. 24, 1998, now U.S. Pat. No. 5,928,128, which claims priority to Provisional Application Ser. No. 60/041,691; filed Mar. 25, 1997.

FIELD OF THE INVENTION

The present invention relates to the real time measurement of a fluid volume in a blood filter, and more particularly to measurements of blood volume and changes in blood volume in a filter.

BACKGROUND OF THE INVENTION

In a large number of medical procedures, at least a portion of the blood volume is passed through a filter. The filter is designed to remove certain particulate matter from the blood. Alternatively, the filter may be designed to remove specific chemicals and water solutions during the filtering process.

A typical device that exposes blood to a filter is a dialyzer. One of the main parameters of filter quality is filter blood volume (FBV). In terms of the dialyzer, the filter blood volume is often referred to as dialyzer blood volume (DBV). Alternatively, the volume has been referred to as fiber bundle volume. The term filter blood volume (FBV) will be used to encompass all the filter constructions including filters having plates, fibers or biological cells.

Due to the exposure to the blood, clotting may occur in the filter and thereby significantly decrease the surface area of exchange available to the blood and hence decrease filtration. In this case the quality of treatment may be jeopardized. Fiber clotting during hemodialysis can significantly decrease the volume of blood for solute exchange.

Filter bundle volume, the total space within the blood compartment of hollow fiber hemodialyzers, correlates closely with dialyzer surface area, a major determinant of solute clearance. A decrease in surface area due to clotting causes a decrease in solute clearance that puts the patient at risk for inadequate dialysis. Since FBV correlates with membrane surface area and is easy to measure in vitro, FBV has been selected, in centers where dialyzer reuse is permitted, as the main criterion that allows a dialyzer to be reused. In countries where reuse of dialyzers is permitted, the main criteria for reuse is comparison of current FBV to its initial value. Traditionally, FBV is measured after cleaning, clot removal, and pressure flushing. The FBV values determined by this traditional process may not represent the actual FBV.

The sequence of procedures for dialyzer reuse consists of cleaning, including flushing the fibers with pressurized water to remove clots and debris, and measurement of FBV by volumetric displacement of air or liquid which is compared with the original dialyzer volume. Because vigorous flushing removes much of the clot, FBV measured in vitro may not represent the true in vivo volume and the corresponding surface area available for solute exchange.

As the filters must be monitored and changed, the filters are usually disposed extracorporeal. The relationship of a filter to a particular medical procedure is sensitive to a variety of parameters. Generally, the operating pressure, or resistance of a filter must be within particular predetermined limits.

However, as the filter is often removing material that is not perceptible to the naked eye, it is general practice to remove the filter from the fluid circuit and fill the filter with water to determine the filter volume. This process is not only time consuming, but exposes the filter to contamination. Also, the interruption of the filtering process can be detrimental to the treatment of the patient. For example, in procedures such as hemodialysis, a filter is used to remove selected particles and liquids from the bloodstream of the patient.

Difficulties in making such measurements have resulted from the fact that such procedures usually involve extracorporeal circulation of the blood from a patient through, for example a blood treatment system, and in many cases the effects of the system itself on the blood flow or on the measurement devices is unknown. For example, if blood is directed to a dialysis filter through plastic tubing, the effect of the plastic material on measuring equipment using ultrasound waves may not be known with any certainty, since characteristics of the material can vary from one tube to another.

There is emerging technology of locating a blood filter inside the patient. However, even these filters are subject to the traditional concerns of proper functioning. If the filter is inserted into the body, then the measurements are made using sensors mounted on a blood vessel.

Therefore, the need exists for a method and apparatus for monitoring the FBV. A need also exists for the real time monitoring FBV. A need further exists for measuring the FBV during use or when the filter is not in use, wherein the FBV volume has improved accuracy. The need also exists for monitoring a change in the FBV to allow adjustments to the procedures to accommodate or correct such volume changes.

SUMMARY OF THE INVENTION

It is an object of the present invention to provide a method and apparatus for accurately and reliably measuring filter blood volume in a filter. The filter may be a patient filter in the patient, extracorporeal, in a separate machine, dialyzer, or in a testing procedure of the filter in a separate machine, such as a reuse machine. In the separate testing procedures, the FBV be determined with any liquid. Therefore, blood not is required to determine the FBV. The present invention also allows for FBV determination and particularly externally of the vein or artery, or in tubing leading to a blood treatment system which carries the blood exteriorly of the body of the patient.

It is another object of the present invention to measure a filter blood volume by measuring an induced dilution in the blood and monitoring passage of the dilution.

Generally, the present invention relates to a method and apparatus for measuring or monitoring the volume of a blood side of a filter by one of (i) employing a bolus injection in the blood side upstream of the filter; (ii) changing the filtration rate in the filter, or (iii) employing a bolus injection in the dialysate side.

Briefly, in the bolus injection configuration, a bolus is introduced in the blood side upstream of the filter during operation of the filter. A downstream signal corresponding to passage of the bolus downstream of the filter is obtained. Further, a blood flow rate through the filter determined. Finally, the blood volume of the filter is calculated in response to the downstream signal and the determined blood flow rate. In a preferred embodiment, the bolus is introduced in the blood side upstream of the filter sufficiently near the filter to substantially preclude compensation of the downstream signal.

In the filtration rate change embodiment for monitoring of a volume of blood in a dialysis blood filter during operation of the filter, a blood parameter is measured downstream of a blood side of the filter; a blood flow rate through the blood side of the filter is determined; the filtration rate is changed to change the blood parameter; and the blood volume is calculated in response to the change of the blood parameter and the determined blood flow rate.

In the bolus injection in the dialysate side embodiment, the filter blood volume is calculated from the introduction and passage of a diffusable and non diffusable indicator through the blood volume and the dialysate volume.

The present invention includes, in part, injecting a volume of a diffusable indicator into a blood flow, wherein the diluting effect of the indicator over a period of time is accurately determined by a sensor, and these changes can be used to calculate the blood volume. The sensor is positioned downstream of the injection so that the indicator passes the sensor, with the measured diluting effect being used to determine various blood parameters. The present invention may employ the relationship between the velocity of ultrasound in blood and the constituents of the blood. That is, the velocity of ultrasound in blood is a function of, among other things, the proteins and ions contained in the blood, with the sound velocity increasing with an increase in protein concentration. Accordingly, the velocity of sound through a blood sample can be varied by diluting the blood with an indicator having different acoustical characteristics than those of the blood; for example, through the use of a saline solution that has no proteins.

The present invention provides a relatively simple technology for measuring the volume of a blood filter and creates an opportunity to control filter and dialyzer performance and give an early warning of clotting to improve the quality of a variety of procedures including hemodialysis.

BRIEF DESCRIPTION OF THE DRAWINGS

FIG. 14 is a schematic view of a portion of the system showing a further apparatus for monitoring filter blood volume in a blood filter during operation of the filter, the blood filter having a blood side and a dialysate side having a known volume.

FIG. 15 is a schematic view of a portion of the system showing a further apparatus for monitoring filter blood volume in a blood filter during operation of the filter, the blood filter having a blood side and a dialysate side.

DETAILED DESCRIPTION OF THE PREFERRED EMBODIMENTS

U.S. Pat. No. 5,453,576 (N. Krivitski) is hereby expressly incorporated by reference.

The Apparatus

Figure 1:
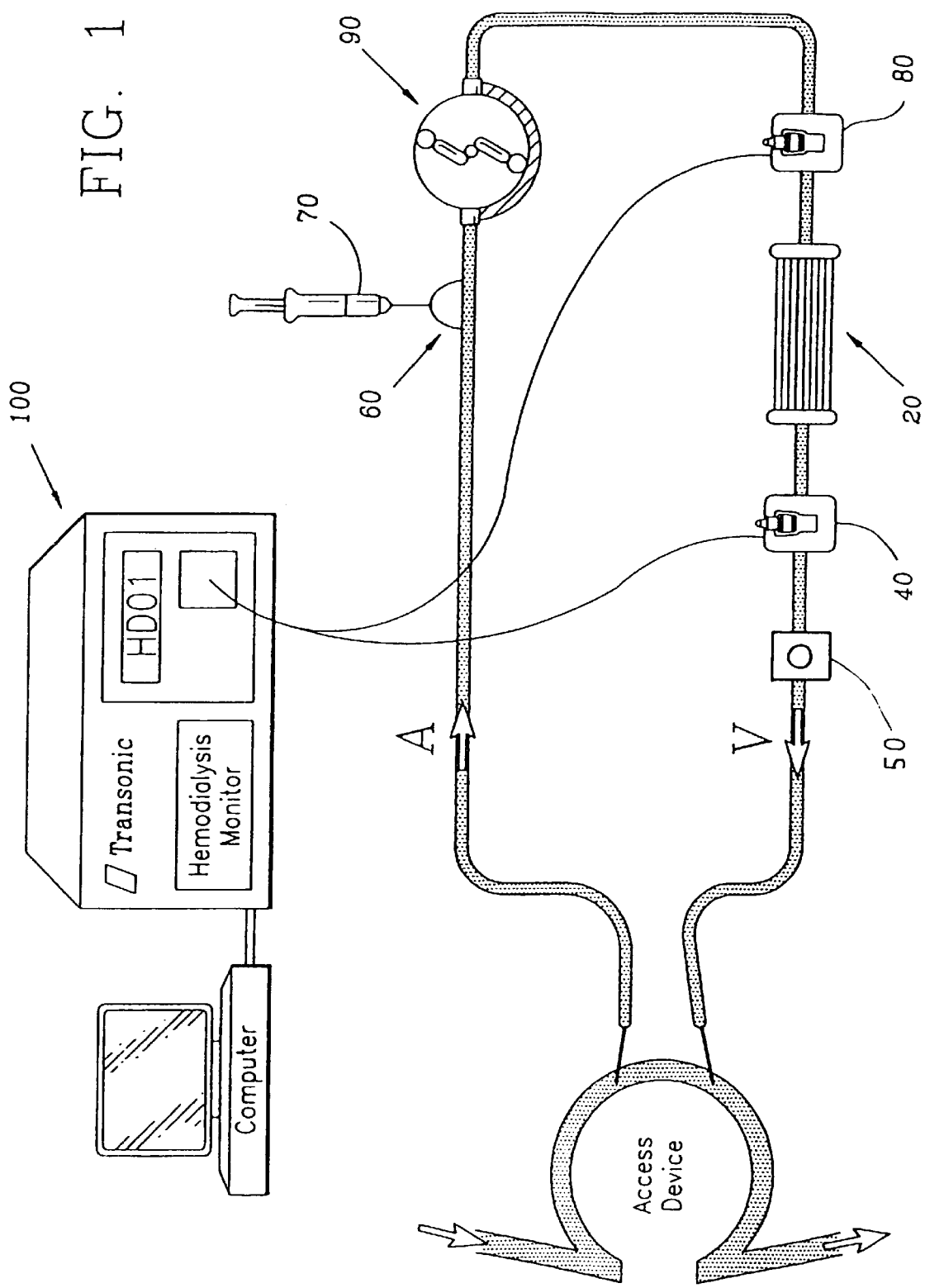
FIG. 1 is a system view of a filter incorporated in a circulation system and an apparatus for measuring filter blood volume.

FIG. 1 discloses a schematic diagram having the main components of a circulation system for passing blood through a filter. The apparatus for calculating and monitoring a change in filter blood volume may include a filter 20, a venous dilution sensor 40; a venous flow rate sensor 50; an injection port 60; an injectable indicator 70; an arterial dilution sensor 80; a pump 90; and an evaluating device 100. As discussed, the invention may be practiced with an arterial flow rate sensor in place of or in addition to the venous flow rate sensor 50. Depending upon the particular configuration, the dilution sensor 40, 80 may be used to also calculate the respective blood flow rate, thereby removing the need for a separate flow rate sensor.

Referring to FIG. 1, "A" is designated as the arterial side and "V" is designated as the venous side. The term "upstream" is used to designate a portion of the circulation system from which the fluid flows with respect to a given position. Similarly, the term "downstream" designates a portion of the system to which fluid will flow from a given position.

The present system provides the real time calculating and monitoring of volume of the filter 20. The relevant volume of the filter 20 may be referred to as the filter blood volume (FBV) or the dialyzer blood volume (DBV) or fiber bundle volume, depending upon the configuration of the particular filter. The filter 20 may include a single, or a plurality of tubes, plates, a conglomeration of biological cells or fibers across which a pressure differential is created. Each configuration creates a volume in a filter 20, the FBV, which may experience a volume change in response to changes in blood characteristics within the filter or due to the pressure change and filtration rates. The term "blood side" of the filter 20 designates the portion of the filter through blood flows and the term "dialysate side" of the filter designates the portion of the filter through which dialysate flows, wherein during operation of the filter selective components of the blood may pass from the blood side to the dialysate side or vise verse.

The filter 20 may be in the form of a dialyzer having an inlet 22, a membrane through which a blood component may pass, and an outlet 24. A particular dialyzer may be that sold by Baxter as CA-110, CF-25; Fresenius F80A, F80B; or Amicon Diafilter-30. It is understood the dialyzer may be a filter 20 of a dialysis type that employs a pressure differential, diffusion or osmosis to cause molecules of a given size to pass through a membrane, or a filter that chemical or physically attaches to certain components in the blood.

The evaluating device 100 may be personal computer capable of curve plotting and performing the calculations set forth in the present application. The evaluating device 100 receives signals from the sensors and generates values representing flow rates and volumes and is capable of determining a mean transit time through the filter 20.

The present invention may include a feedback system for selectively triggering an alarm, upon a predetermined change in the measured volume of the filter or heparin infusion or other anticogulant or other treatment substance. Alternatively, the alarm may be triggered by a change in the volume, independent of the measured volume.

The venous and arterial dilution sensors 40, 80 detect a blood parameter or property, and particularly variations of the blood parameter or property.

Thus, the sensors 40, 80 are capable of sensing a change is a blood property, parameter or characteristic. For purposes of the disclosure the sensors 40, 80 may be referred to as dilution sensors, but this label is not intended to limit the scope of available sensors. Ultrasound velocity sensors as well as temperature sensors and optical sensors, density or electrical impedance sensors, chemical or physical sensors may be used to detect changes in blood parameters. It is understood that other sensors that can detect blood property changes may be employed. The operating parameters of the particular system will substantially dictate the specific design characteristics of the dilution sensor, such as the particular sound velocity sensor. The venous and arterial dilution sensors 40, 80 may be identical components. The venous and arterial dilution sensors 40, 80 are operably connected to the evaluating device 100. The dilution sensors 40, 80 may be sound velocity sensors and any of a variety of readily available commercial devices, such as HD01 Hemodialysis monitor manufactured by Transonic Systems Inc. Ithaca N.Y.

The dilution sensors 40, 80 are selected to identify the passage of a bolus past the respective sensor. The term "bolus" is defined as any change in a blood property, parameter or characteristic, and may include changes such as step functions and curvilinear dependencies. The bolus may affect any of a variety of blood characteristics including protein concentration, electrical impedance, temperature, optical properties, sound velocity, hematocrit, chemical properties, and physical properties including blood density.

A number of indicators 70 are capable of creating a bolus. The indicator 70 is preferably injectable and may be any of the known indicators including saline solution or any other solution that changes blood properties that can be detected by the dilution sensors. The injectable indicator 70 may be introduction of temperature gradient or another blood property changes without introduction additional volume or other blood parameter, as well as a withdrawal of substances from blood. Preferably, the indicator is non toxic with respect to the patient if used during a treatment procedure. The injected indicator 70 thus forms a bolus.

Depending upon the particular configuration of the system, as described herein, the dilution sensor 40 is coupled to at least an venous portion of a blood system for detecting the dilution of the blood, identifying a dilution curve. If the arterial dilution sensor 80 is employed, it is operably connected to the arterial line and the venous dilution sensor 40 is operably connected to the venous line. Ultrasonic sensors measure sound velocity dilution as the indicator is carried past the sensor by the bloodstream, and changes in sound velocity are plotted to permit calculation of various blood parameters. The time at which the indicator reaches the sensor after injection, the area under the plotted curve representing the changes in sound velocity at the sensor, and the amplitude of the measurement all provide information concerning the blood characteristics.

The injection port 60 is located in the circulation system to allow selective access to the blood flow. The injection port 60 may be any of a variety of constructions allowing single or repeated access to the blood flow. For example, the indicator 70 may be introduced into arterial injection port 60 before the filter 20. Preferably, the indicator 70 is injectable through the injection port 60.

The flow sensors are used to measure the flow rate in the local section of the circulation system. The flow rate sensors provide output signals corresponding to blood flow measurement. Each of the blood flow sensors may be a Bypass Flow Meter model HT 109 or model T106 produced by Transonic Systems, Inc., Ithaca, N.Y., for example. However, it is understood the dilution sensors may generate sufficient signals to permit measurement of the respective blood flow and thereby obviate the necessity of a given flow sensor.

As an example of the dilution sensor 40 functioning, it is recognized that the velocity of ultrasound in blood is a function of, among other things, the proteins and ions contained in the blood, with the sound velocity increasing with an increase in protein concentration. Accordingly, the velocity of sound through a blood sample can be varied by diluting the blood with an indicator having different acoustical characteristics than those of the blood; for example, through the use of a saline solution that has no proteins. By injecting such an indicator 70 into a blood flow, the diluting effect of the indicator over a period of time can be accurately determined by the sound velocity sensor which is responsive to changes of sound velocity in the blood.

The dilution measurements can be made in an extracorporeal portion of the circulation blood system in which clamp-on sound velocity sensors are secured for example, to tubing leading to exterior blood treatment equipment such as the hemodialysis machine, or the like as shown in FIG. 1. In such an embodiment, referred to as a clamp-on measurement system, measurements of blood are made outside the patient's body; for example, in extra corporeal tubing leading from the vascular system of the patient to a blood treatment system such as a dialysis machine. In such a system, blood is drawn from the patient, passed through suitable tubing to a dialysis filter and is then returned through tubing to the patient, but downstream of the withdrawal site. Clamp-on sensors such as ultrasonic flow meters manufactured by Transonic Systems of Ithaca New York are suitable for measuring blood flow through the tubing.

The Method

Generally, the present invention relates to methods and apparatus for measuring or monitoring the volume of a blood side of a filter 20 by employing one of a bolus in the blood side upstream of the filter; changing the filtration rate in the filter; and employing a bolus in the dialysate side.

The basis of the FBV calculations is generally based upon particular indicator movement through the filter 20. The basis of these calculations are set forth.

Theoretical Analysis.

When flow in the system (Q) can be measured accurately, the volume (V) of the system is determined by the following equation [5]:

$$V = Q \times MTT \quad \text{Eq. 1}$$

where MTT (mean transit time) is the average time that the indicator travels through the system. Two methods, one based on a bolus injection of normal saline and the other based on a step change in filtration rate of the filter, were employed for measuring the FBV. The "filtration rate" of the filter is the rate at which a particular material passes from the blood side to the dialysate side. The step change in filtration rate may be accomplished by turning the filter on or off, or changing the rate at which matter crosses the filter.

Bolus Injection Method

Figure 2:
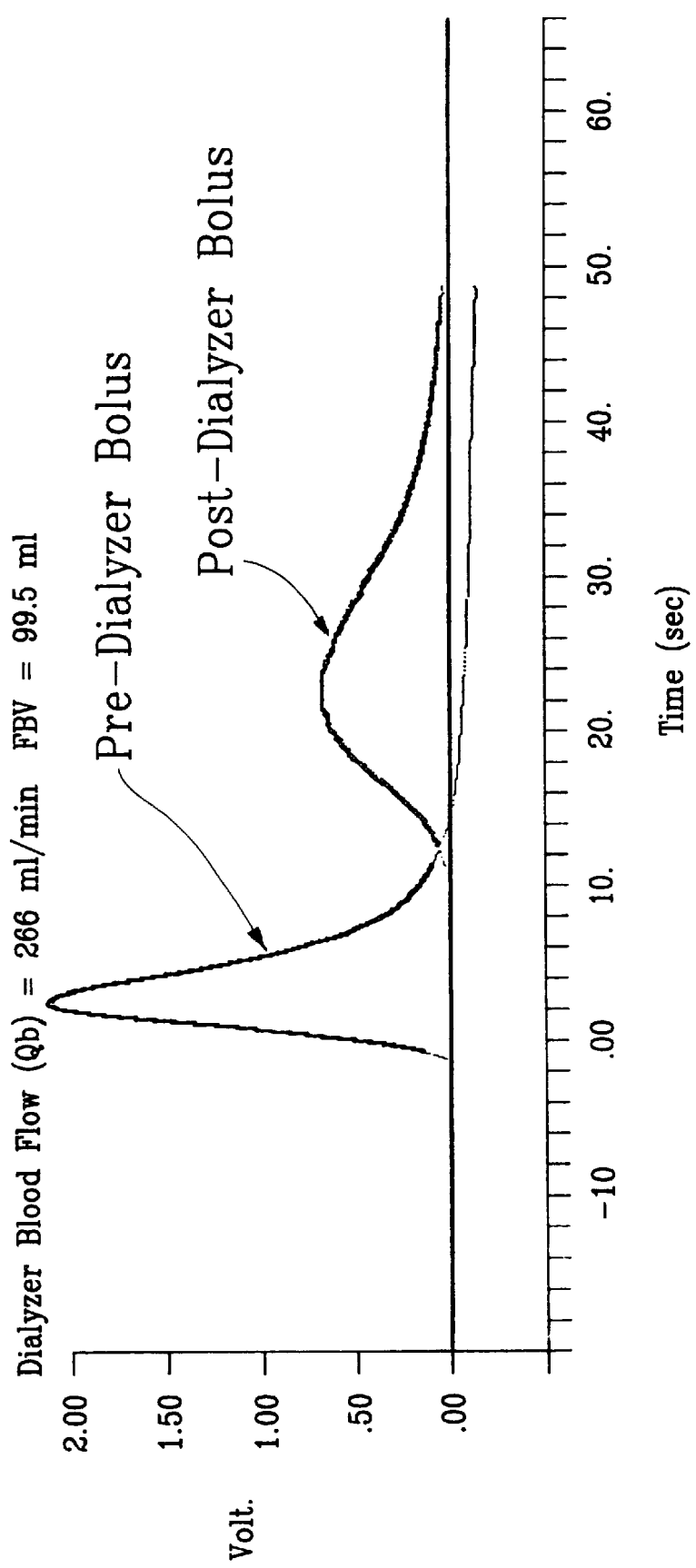
FIG. 2 is a set of the dilution curves recorded by an arterial (pre-filter) ultrasound sensor and a venous (post-filter) sensor following an injection of a bolus into the arterial (filter inflow) blood line.

Equation 1 assumes that the time required for injection of the bolus is negligible, that the bolus was introduced just before the inlet to the dialyzer and that a dilution curve was recorded by the ultrasound sensor immediately at the outlet to the filter. To eliminate the influence of the injection time and the distance between the site of injection and the filter entrance, an additional dilution sensor was placed on the blood inlet side of the filter as shown in FIG. 1. To account for a finite injection time using the two sensors, Equation 1 must be modified. For filtration through the filter turned off (a) and on (b):

$$FBV = Q_b \times (MTT_v - MTT_a) \quad \text{Eq. 2a}$$

$$FBV = (Q_b - 0.5 Q_f) \times (MTT_v - MTT_a) \quad \text{Eq. 2b}$$

where Qb is blood flow through the dialyzer; Qf is the filtration flow rate; MTTv and MTTa are mean transit times of bolus (indicator) recorded by, the sensors placed after the filter (venous line) and before the filter (arterial line) respectively. The formulas for calculating MTT using this bolus injection method are [4]:

$$MTT_a = \frac{\int Ca(t) t \, dt}{\int Ca(t) \, dt} \quad \text{Eq. 3}$$

$$MTT_v = \frac{\int Cv(t) t \, dt}{\int Cv(t) \, dt} \quad \text{Eq. 4}$$

where Ca(t) and Cv(t) are the concentration dilution curves recorded by the arterial and venous sensors, as shown in FIG. 2.

Filtration Method (Step Change)

Figure 3:
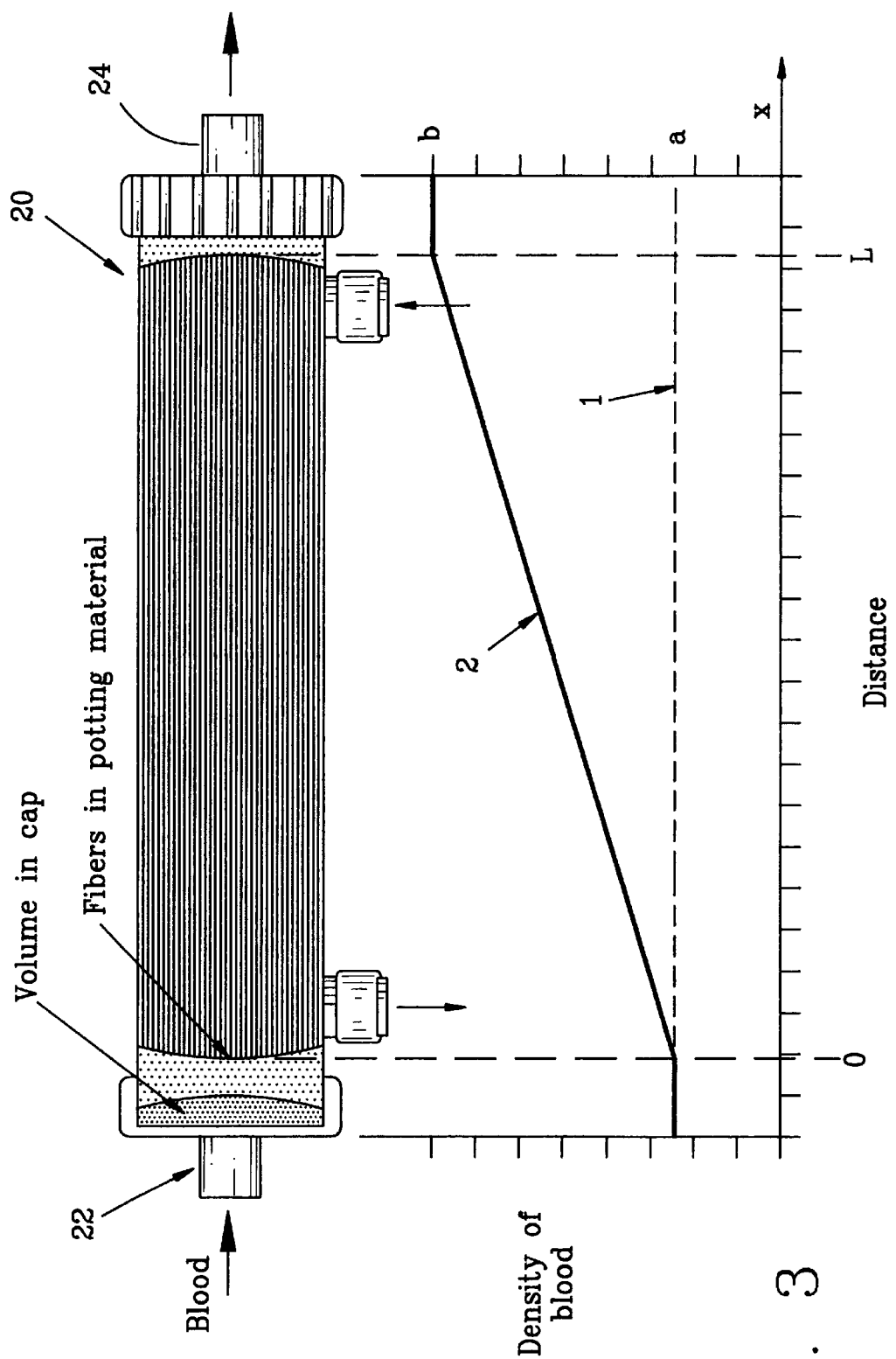
FIG. 3 is a schematic showing expected changes in blood concentration along the dialyzer fibers due to a change in the filtration rate of a filter.

The most convenient way to change blood properties (blood density, hemoglobin concentration, hematocrit, etc.) to allow measurement of volume, is to create a step change in the rate of filtration. When hydrostatic pressure is applied at the filter membrane, creating a gradient from the blood side to the dialysate side, the cells and macromolecules in the blood are concentrated by continuous removal of filtrate from the entire filter blood compartment. This maneuver is analogous to simultaneously adding indicator to the entire filter blood compartment. Referring to FIG. 3. When a steady state is reached, the blood at the entrance of the filter will be less concentrated than at the exit where it is most concentrated. These conditions differ from the traditional well developed methods for constant indicator infusion where, at steady state, the concentration in the system is the same in all locations.

Figure 4:
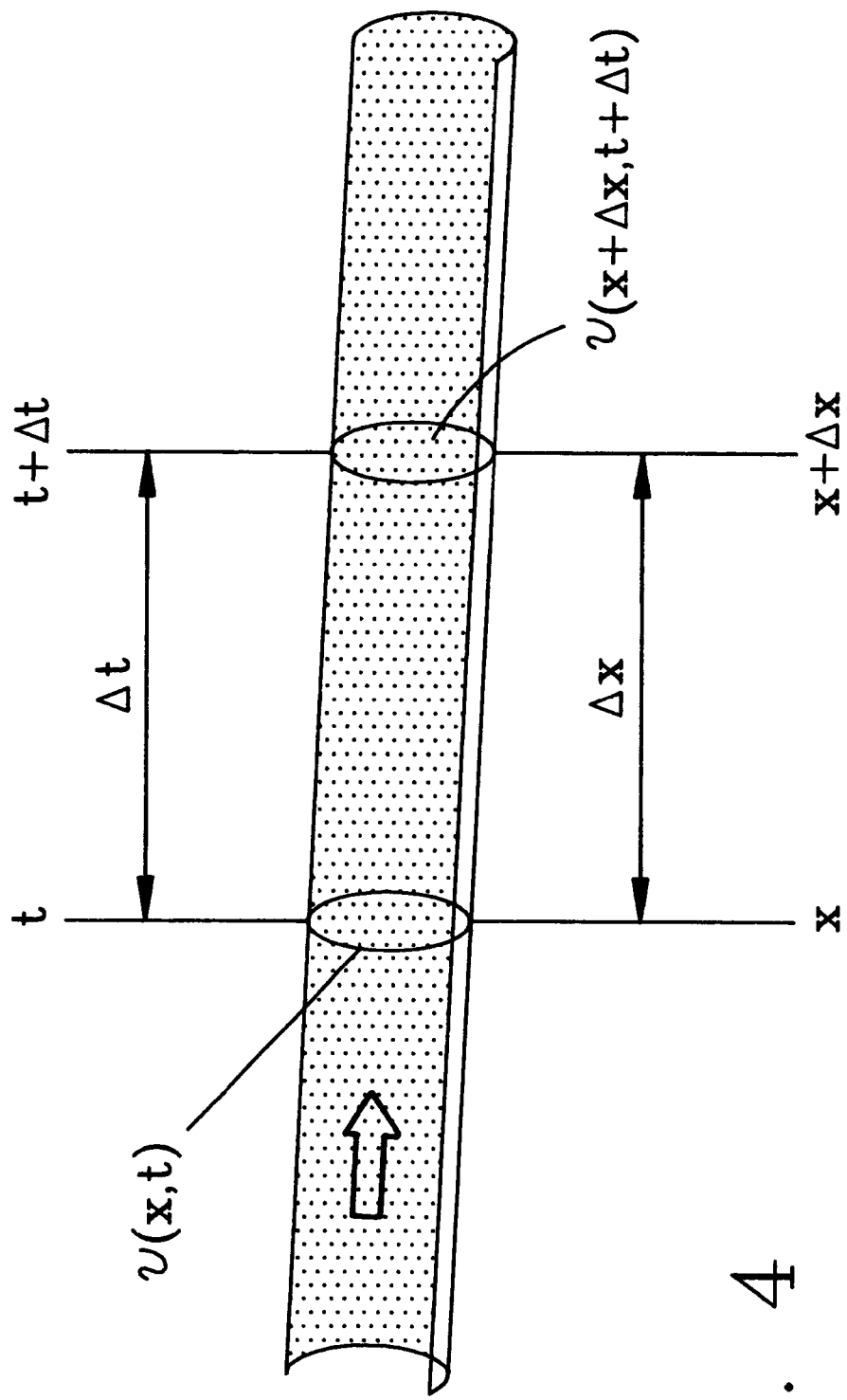
FIG. 4 is a single fiber fluid removal model.

The absence of an analytical formula for the relationship between outflow concentration and FBV required development of a theoretical model of changes in blood concentration at the dialyzer blood outlet in response to a step change in filtration. The analysis was performed in two steps. First, the outflow concentration in a single fiber, as shown in FIG. 4, was evaluated after a step change in the filtration rate. Liquid flow balance and mass balance for non-removable blood particles in the fiber were used to develop the differential equations. Second, the results obtained for one fiber were expanded to the whole dialyzer with the assumption that the fractional removal of filtrate from the blood compartment is the same for all fibers that take part in filtration.

Specifically, it was assumed that fractional removal of fluid (F) was uniform throughout the volume of blood in the filter and in the fibers.

$$F = Qf/FBV [\text{ml/sec/ml} = 1/\text{sec}] \quad \text{Eq. a1}$$

Single Fiber Analysis

Single fiber concentration changes are schematically shown in FIG. 4. After filtration is turned on, the change in concentration within a single fiber is calculated based on liquid flow balance and non removable particles balance. Liquid flow balance provides:

$$v(x) \times S = v(x + \Delta x) \times S + F \times \Delta x \times S \quad \text{Eq. a2}$$

where v(x) is the average linear velocity of liquid at point x; S is the cross sectional area of the fiber; F is the fractional rate of filtration in the fiber, from Equation a1.

The second of the two terms summed in Equation a2 represents the flow of filtrate removed from the fiber as the blood flows along the distance Δx. Equation a2 may be rewritten in differential form:

$$v'(x) = -F \quad \text{Eq. a3}$$

The solution of this equation is:

$$v(x) = v^* - F \times x \quad \text{Eq. a4}$$

where v* is the average linear velocity of blood at the entrance to the fiber.

From a consideration of mass balance for non removable blood particles:

$$C(x,t) \times v(x) = C(x + \Delta x, t + \Delta t) \times v(x + \Delta x) \quad \text{Eq. a5}$$

where C(x,t) is the concentration of non removable blood particles (red blood cells, hemoglobin's etc.)

The relationship between $\Delta x$ and $\Delta t$, as $\Delta x$ and $\Delta t \to 0$, may be expressed, as:

$$\frac{\Delta x}{\Delta t} = v(x) \qquad \text{Eq. a6}$$

This means that the movement of particle packet is being recording. Decomposing the right part of Equation a5 in a Taylor series gives:

$$v(x+\Delta x)=v'(x)+v'(x)\times\Delta x \qquad \text{Eq. a7}$$

$$C(x+\Delta x, t+\Delta t) = C(x, t) + \frac{\partial C(x, t)}{\partial x} \times \Delta x + \frac{\partial C(x, t)}{\partial t} \times \Delta t \qquad \text{Eq. a8}$$

Combining Equations a5–a8 with consideration of Equation a3 and neglecting small values of the second order gives:

$$C(x, t) \times F = C(x, t) + \frac{\partial C(x, t)}{\partial x} \times v(x) + \frac{\partial C(x, t)}{\partial t} \qquad \text{Eq. a9}$$

Before filtration is turned on, the concentration of non-diffusable particles was the same along the entire fiber (Equation a10) and was equal to the entering (initial) concentration Co that was considered constant during the measurement (Equation a11):

$$C(x,0)=Co \ L \geq x \geq 0 \qquad \text{Eq. a10}$$

$$C(0,t)=Co \qquad \text{Eq. a11}$$

Because the concentration sensor is located at the exit of the filter the particular interest was in the outflow concentration at x=L, as shown in FIG. 3. The solution of Equation a9 consists of 2 parts. The first part is related to the concentration of blood that was in the fiber at the moment when filtration was turned on. The second part is related to the blood that enters the filter after filtration was turned on and reaches location x=L at time $t^*$ after passing through the entire fiber. After this moment, the process in this fiber achieves a steady state. The first part of the solution for $t<t^*$:

$$C(L,t)=C(L,0)\times\exp(F\times t)=Co\times\exp(F\times t) \qquad \text{Eq. a12}$$

The second part of the solution for $t>t^*$ for x=L:

$$C(L, t) = Co \times \frac{1}{1 - F \times \frac{L}{v^*}} \qquad \text{Eq. a13}$$

Equation a12 gives the concentration changes during the transfer process and depends only on time "t" and F. It is also clear from Equation a12 that the concentration will be the same for any fiber in the dialyzer at moment "t". Equation a13 gives the concentration during the steady state and does not depend on time. The outflow concentration of every fiber will depend on $v^*$, the average linear velocity of liquid at the fiber entrance that may be different for every fiber due to different inner diameters. So in contrast to Equation a12 the outflow concentration at $t>t^*$ may be different for every fiber.

In the second step, the analysis is applied to the entire filter concentration changes. The resulting concentration in the filter outflow, Cv(L,t), is the sum of outflow concentrations in all fibers multiplied on their flow and divided by total flow:

$$Cv(L, t) = \frac{\sum C_n(L, t) \times S_n \times v_n^*}{\sum S_n \times v_n^*} \qquad \text{Eq. a14}$$

where n=1 ... n; n is the number of fibers in dialyzer; $C_n(L,t)$ is the outflow concentration of the "nth" fiber; $S_n$ is the cross sectional area of the "nth" fiber; $v_n^*$ is an average line blood flow in the "nth" fiber.

It is clear from Equation a12 that the outflow concentration in Equation a14 in every fiber at time "t" is the same until the moment when, in one of the fibers, $t>t^*$:

$$C_n(L,t)=Co\times\exp(F\times t) \qquad \text{Eq. a15}$$

For dialyzer outflow:

$$\Sigma S_n \times v_n^* = Q_b - Q_f \qquad \text{Eq. a16}$$

Considering Equations a12, a15 and a16, Equation a14 may be simplified for any $t<t^*$:

$$C_v(L,t)=Co\times\exp(F\times t) \qquad \text{Eq. a17}$$

Figure 5:
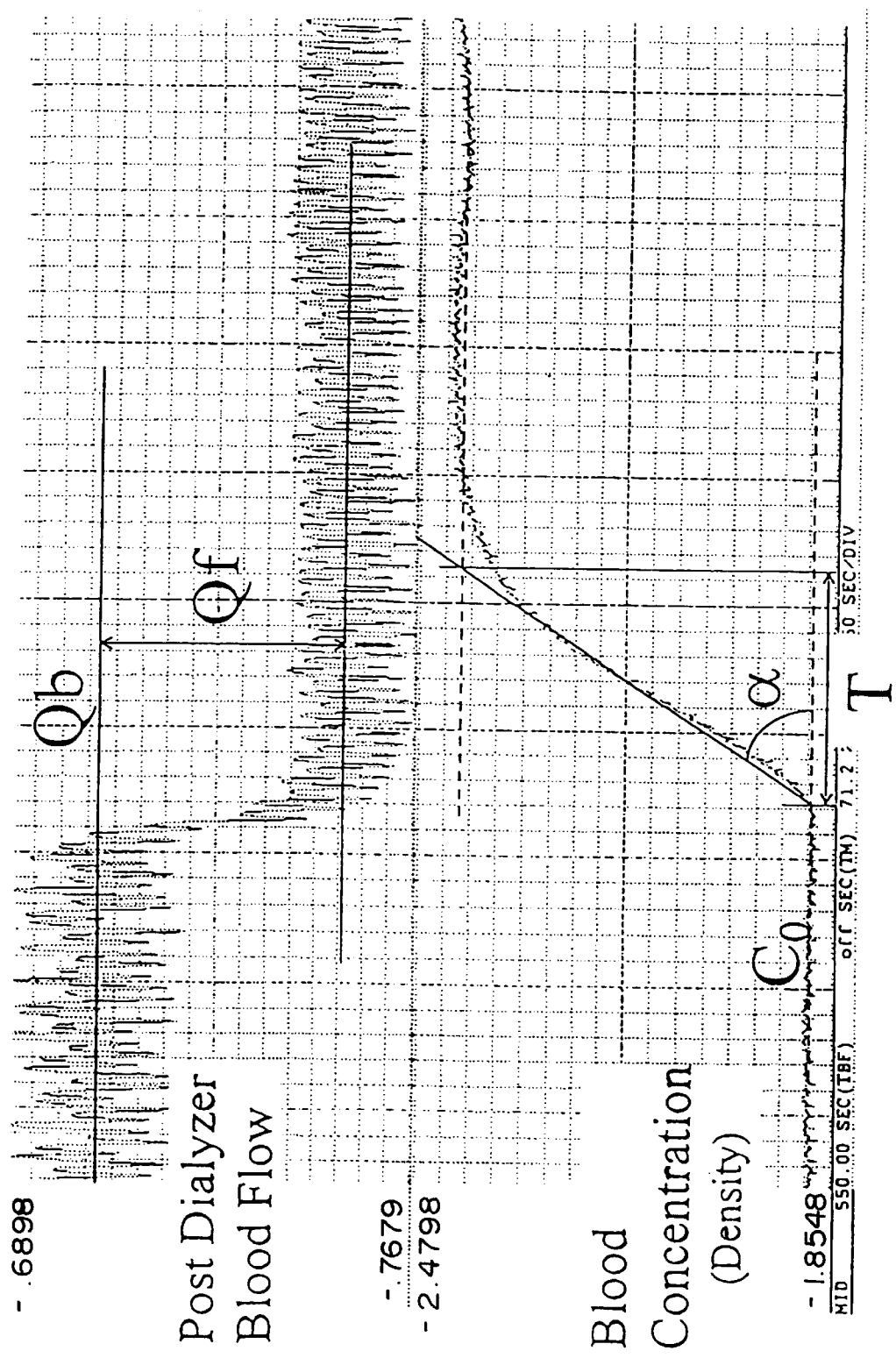
FIG. 5 is a time tracing showing dialyzer blood flow recorded by an outflow sensor and showing coincident with a change in the filtration rate a rise in blood concentration recorded by the outflow sensor.

Equation a17 for the entire filter is the same as for one fiber. This condition exists until, in any single fiber, the blood that enters the fiber after filtration was turned on reaches x=L (i.e., it passes through the entire length of the fiber). Estimating the practical value of exponent F×t, for Qf in the range 10–20 ml/min, dialyzer blood volume 60–120 ml, the estimation of F gives F=0.0014–0.0056/sec. For time t in the order of 7–10 sec, the value of F×t will be in the order of 0.01–0.05<<1. Then with accuracy of less than 1% error, Equation a17 may be rewritten:

$$C_v(L, t) = Co \times (1 + F \times t) = Co \times \left(1 + \frac{Q_f \times t}{FBV}\right) \qquad \text{Eq. a18}$$

and the dialyzer blood volume after filtration is turned on can be calculated from Equation a18:

$$FBV = \frac{Co \times Q_f \times t}{(C_v(L, t) - Co)} \qquad \text{Eq. a19}$$

or $$FBV = Co \times \frac{Q_f}{\tan\alpha} \qquad \text{Eq. a20}$$

where $\tan \alpha$ is calculated from FIG. 5.

Equation a20 can also be represented in a different form to avoid measurement of the absolute concentration Co. The mass balance of large particles that do not diffuse through the filter at steady state may be expressed as:

$$Q_b \times Ca^* = (Q_b - Q_f) \times Cv^* \qquad \text{Eq. a21}$$

where $Ca^*$ and $Cv^*$ are concentrations of large particles in the filter arterial and venous blood at steady state, respectively.

Before filtration is turned on or changed, the initial concentration in the venous line is the same as in the arterial line (Co=Ca). The initial venous concentration, Co, will be the same as $Ca^*$ at steady state if Ca does not change during transfer time Ttr. A change in Ca may occur if the concentration change introduced by a change in filtration recirculates through the dialyzer (FBV), through the arterial and venous tubing (Vav), and then through the cardio-pulmonary system (Tcp) before a steady state is reached. Ttr can be estimated based on existing tubing systems and dialyzers:

$$Tr \cong \frac{(V_{av} + FBV)}{Q_b + T_{cp}} \qquad \text{Eq. a22}$$

The quickest return (worst case scenario) in the absence of access recirculation: Vav=100 ml; FBV=60 ml; Qb=500 ml/min; Tcp=10 sec, gives Ttr=30 sec. This time is sufficiently long to allow a steady state to be reached across the dialyzer.

For these conditions, Equation a21 may be rewritten (Ca*=Ca=Co):

$$Cv^* - Co = Cv \times \frac{Q_f}{Q_b} \qquad \text{Eq. a23}$$

Finally, from Equation a20, substituting tan $$\alpha = \frac{(Cv^* - Co)}{T}$$

(as shown in FIG. 5, and considering Equation a23, the formula for FBV when filtration is turned on is:

$$FBV = (Q_b - Q_f) \times T \qquad \text{Eq. a24}$$

When these measurements were performed by turning filtration off instead of turning it on, the initial steady state concentration along the dialyzer will be similar to that shown in FIG. 3. The equation for concentration in a single fiber before filtration is turned off is (see Equation 13a):

$$C(x, t = 0) = Co \times \frac{1}{1 - F \times \frac{x}{v^*}} \qquad \text{Eq. a25}$$

where t=0 signifies the time at the beginning of the process, and v* is the same at any place in the fiber. The fiber outflow concentration at time "t" depends on how far this portion is located (distance L−x) from the exit. The amount of time "t" required for the portion of the blood located at coordinate "x" to reach the fiber exit is:

$$t = \frac{(L - x)}{v^*} \qquad \text{Eq. a26}$$

The outflow concentration from Equation a25 and Equation a26 is:

$$C(L, t) = Co \times \frac{1}{\left[1 - \frac{F \times (L - v^* \times t)}{v^*}\right]} \qquad \text{Eq. a27}$$

A practical estimation of F×t<<1 was described above; the same conditions may be applied to the expression in squared brackets of Equation a27:

$$C(L, t) = Co \times \left[1 + F \times \frac{(L - v^* \times t)}{v^*}\right] \qquad \text{Eq. a28}$$

or $$C(L, t) = Co \times \left[1 + F \times \frac{L}{v^*}\right] - Co \times F \times t \qquad \text{Eq. a29}$$

The first part of the sum is the outflow concentration in the fiber at steady state before filtration is turned off (or changed). The resulting filter outflow concentration Cv(L,t) is the sum of outflow concentrations in all fibers (Equation a29) multiplied by their individual flows and divided by the total flow (Equation a14). The first part of the sum gives the initial level Cv*:

$$Cv(L,t) = Cv^{**} - Co \times F \times t \qquad \text{Eq. a30}$$

or from Equation a1:

$$FBV = \frac{Co \times Q_f \times t}{(Cv^{**} - Cv(L, t))} \qquad \text{Eq. a31}$$

or by analogy with Equation a20:

$$FBV = Co^* \times \frac{Q_f}{\tan \alpha} \qquad \text{Eq. a32}$$

and also by analogy with Equation a24:

$$FBV = (Q_b - Q_f) \times T \qquad \text{Eq. a33}$$

The resulting formulas for FBV (Equations a20 and a32; Equations a24 and a33) are the same regardless of whether FBV is measured by turning filtration on or by turning it off, or changing the filtration rate.

The fractional removal rate is Qf/FBV. Two modifications of this formula (Equations a20 and a24) were derived for FBV when filtration occurs during dialysis (filtration turned on):

$$FBV = Co \times \frac{Q_f}{\tan \alpha} \qquad \text{Eq. 5}$$

or:

$$FBV = (Q_b - Q_f) \times T \qquad \text{Eq. 6}$$

where Co is the initial concentration, before filtration is turned on as shown in FIG. 5, of non-diffusable substances recorded by the venous sensor; tan and T are calculated from the subsequent changes in concentration. For the case when filtration is turned off see the analogous formulas (Equations a32 and a33).

A change in the FBV may be measured from monitoring a change in the filtration rate, without requiring a measurement of the flow rate through the blood side or the dialysate side. In particular, a first blood parameter measurement is obtained downstream of a blood side of the filter after a first filtration rate change (T1). A second blood parameter measurement is then obtained downstream of a blood side of the filter after a second filtration rate change (T2). Any change in the FBV is calculated from the first blood parameter measurement and the second blood parameter measurement. Specifically, the change in FBV may be determined by $$\frac{\Delta V_B}{V_B} = \frac{T_2 - T_1}{T_1}.$$

Referring to FIG. 5, the change in FBV may also be calculated as $$\frac{\Delta V_B}{V_B} = \frac{(\tan\alpha 2 - \tan\alpha 1)}{\tan\alpha 1};$$

wherein tan α1 is the tangent of the graphic angle formed by the first filtration rate change and tan α2 is the tangent of the graphic angle formed by the second filtration rate change.

Accuracy and Reproducibility

Figure 6:
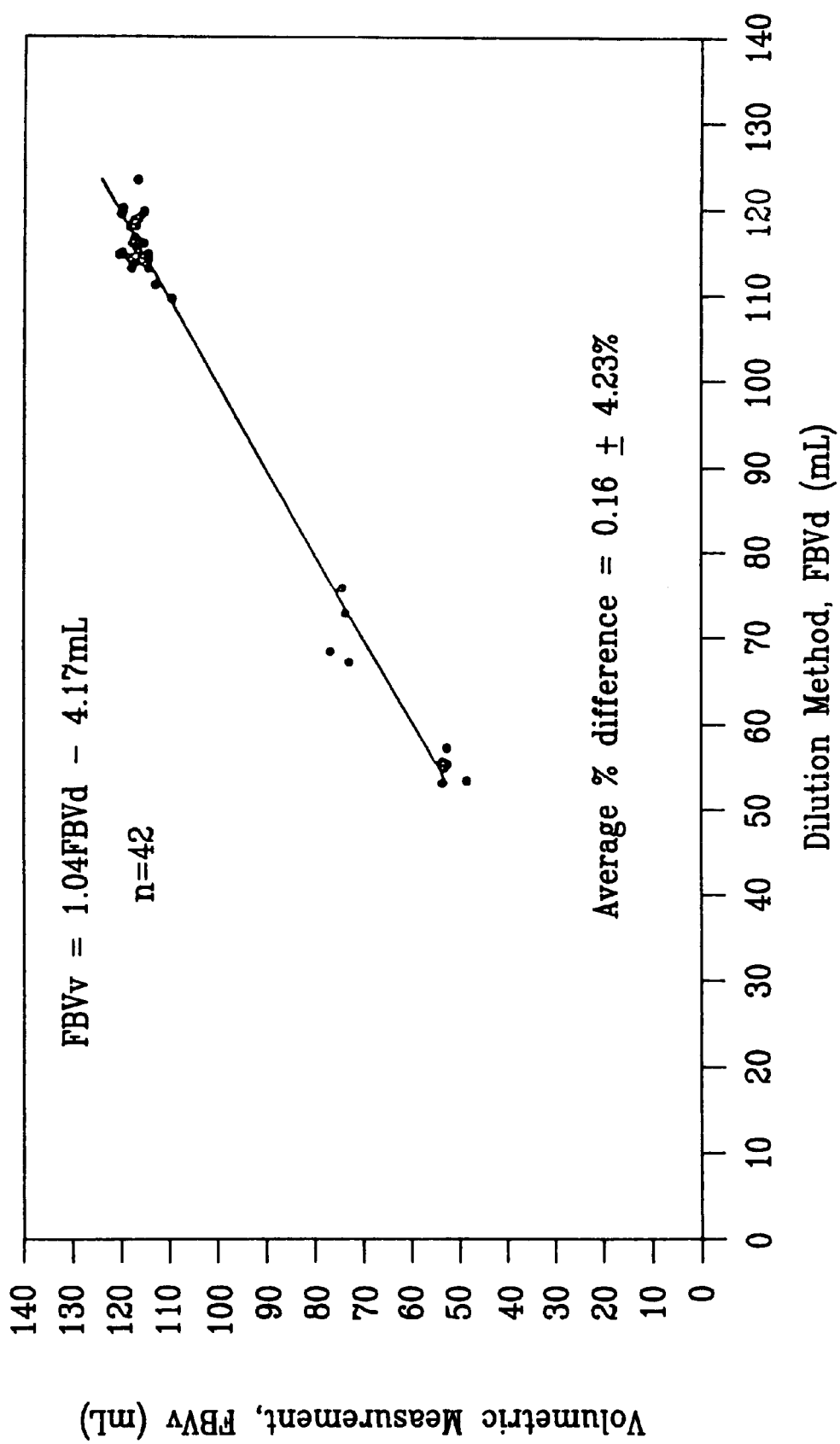
FIG. 6 is a graph showing filter blood volume measurements by volumetric measurement and dilution methods.

The reproducibility of both the bolus and the filtration methods averaged 1% to 4% for both in vitro and in vivo FBV measurements. The bolus method (FIG. 6) showed substantial agreement with volumetric graduated cylinder method measurements (mean error 0.16±4.23%, n=42) while filtration method significantly underestimated FBV when measured volumetrically by the (15% lower, p<0.01).

As the filtration method measures the volume that is directly involved in the filtration process, the results were consistent with expectations. The blood volume in the portion of the fibers imbedded in potting material at both ends of the filter (FIG. 3) as well as the blood volume taken up by the headers does not take part in the exchange process and therefore would not be a part of the filtration measurements. In contrast, this volume is taken into account by the bolus method, by the graduated cylinder method, and by the reuse machine measurements. When a simple geometrical calculation was used to estimate this "inactive" volume the differences between the filtration method and the graduated cylinder method were minor, 2.10±7.26%.

When compared with volumetric measurements (graduated cylinder) and with measurements by the bolus dilution method, FBV measured by the reuse machine was respectively 4% and 5% less. This small discrepancy may be duel to an inability of the reuse machine to completely flush saline from the fibers.

Both the bolus injection and the filtration technologies can be modified for routine clinical measurements of FBV. Sensors may be moved closer to the patient to the optimal position for measuring access flow and access recirculation. For the bolus method the injections into the arterial line can be replaced by a bolus released from the saline bag like a recently described method for access flow measurements. The filtration step change method provides further benefits. The filtration step change method requires only one (post-filter) sensor, it is simpler to perform and to automate and it appears, based on the above discussion, that the volume measured is more pertinent to the clinical consequence of fiber clotting causing a reduction in solute clearance.

Clinical Relevance

Figure 7:
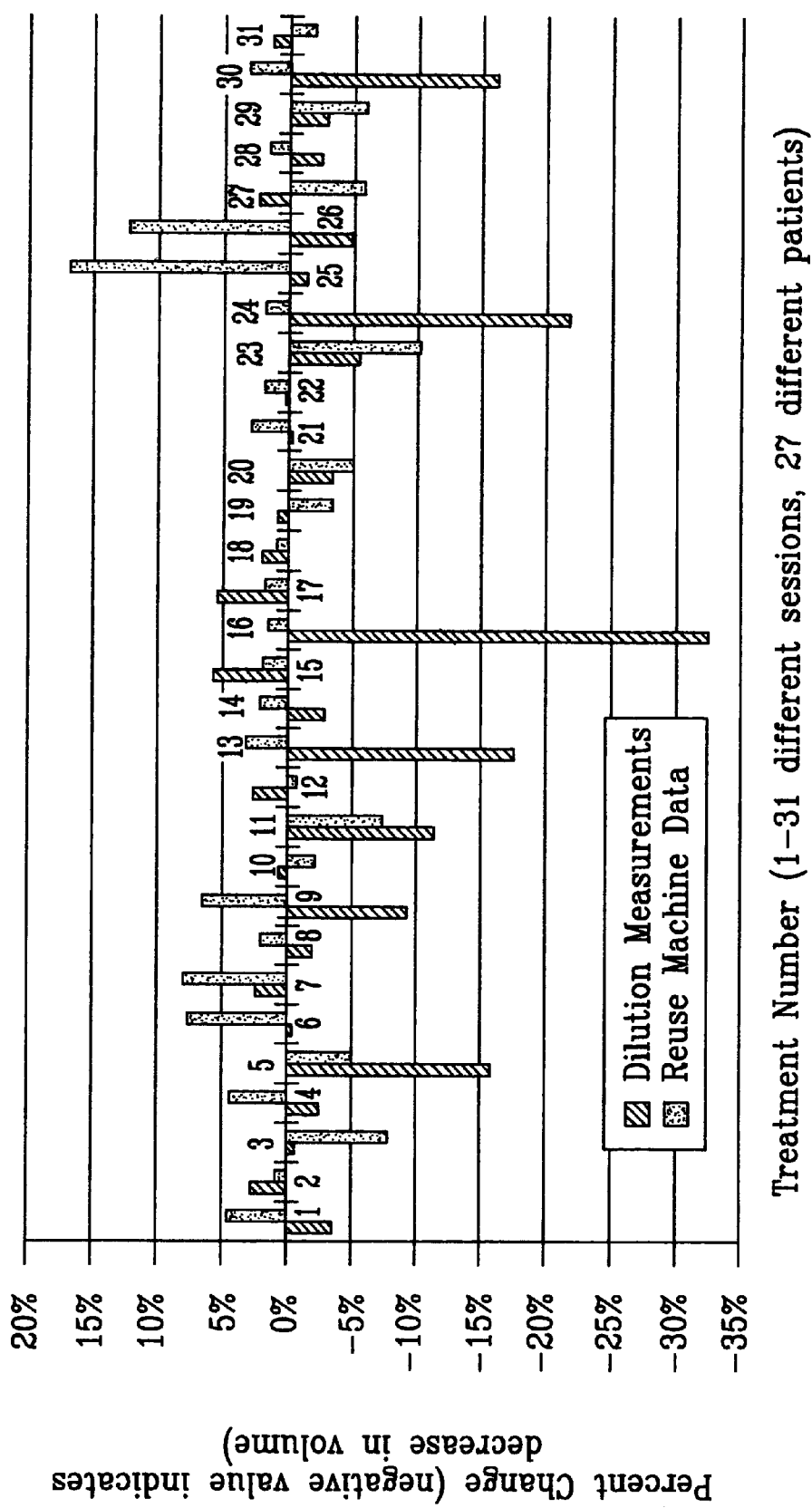
FIG. 7 is a chart of relative change of filter blood volume during dialysis as measured by dilution and by reuse equipment.

The data shown in FIG. 7 suggests that a significant decrease in FBV during dialysis treatments may not be detected by the reuse machine. One must also suspect that in the 6 of 31 treatments where FBV dropped more then 10%, the delivered dose of dialysis was reduced. The discrepancy between FBV measured during dialysis by ultrasound dilution and following dialysis by the reuse machine may be explainable. Specifically, the fibrous threads that result from clotting within the hollow fibers during dialysis are often seen during pressure rinsing of the dialyzer after the session. The observed difference between real FBV during dialysis and assumed FBV measured by the reuse machine may also partly explain results observed by different investigators who examined the effect of dialyzer reuse on performance of the dialyzer.

Possible applications in hemodialysis and hemofiltration for this on-line technology, including treatment for acute renal failure include:

1. Early warning of ongoing clotting for conventional and heparin free dialysis;
2. Quality control of dialyzer reuse;
3. Solute clearance control;
4. Use of machines to measure FBV without requiring the use of blood, such as in reuse machines;
5. Use in filters where biological cells are the filter media; and
6. Optimization of heparin administration.

The theoretical analysis, bench validations, and preliminary clinical data suggest that FBV can be accurately and simply measured by indicator dilution techniques in vivo during hemodialysis and that FBV measured by reuse equipment may not always represent the real dialyzer blood volume during hemodialysis.

Further, it is understood the measurement of FBV may be made when the filter is not actively connected to a patient, or actively filtering. That is, the present invention provides for the testing of filters prior to use, merely upon operatively connecting a filter to the requisite sensors. That is, the present invention may be used in place traditional flushing and volumetric methods.

For purposes of description, it is understood in the following configurations, that the components are operably connected. For example, the sensor 40 is connected to the evaluating device 100, and the sensor is operably connected to the fluid path of the blood flow.

Figure 8:
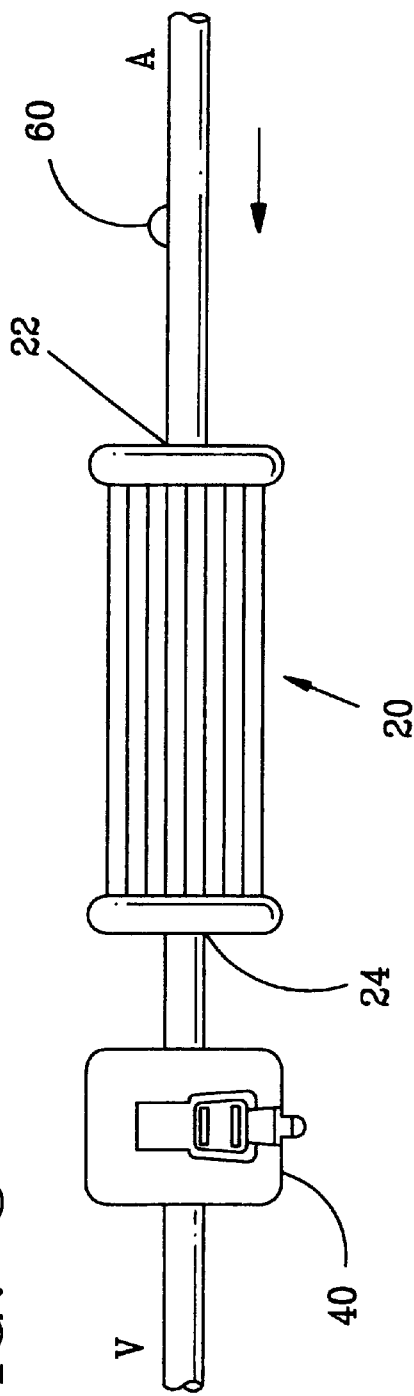
FIG. 8 is a schematic view of a portion of the system showing an apparatus for monitoring a change in filter blood volume during operation of the filter.

Referring to FIG. 8, a configuration for monitoring a change in a volume of blood in a filter 20 during operation of the filter is shown. This configuration includes a dilution sensor 40 in the blood side downstream of the filter 20 and the injection port 60 on the blood side located upstream of the filter. In this system, the method determines a change in the filter blood volume by the relationship:

$$\frac{\Delta V_B}{V_B} = \frac{Q_B(MTT_2) - Q_B(MTT_1)}{Q_B(MTT_1)}$$

where $V_B$ is the blood filter volume; $Q_B$ is the flow rate through the blood filter and MTT is the mean transit time of the respective bolus. For flow rate through the filter being constant, the change in FBV becomes:

$$\frac{\Delta V_B}{V_B} = \frac{MTT_2 - MTT_1}{MTT_1}$$

In operation, a first bolus is injected through the injection port 60 and a first downstream signal is generated as the first bolus passes the dilution sensor downstream of the filter 20. Preferably, the first downstream signal is the mean transit time MTT1 for passage of the first bolus past the dilution sensor 40. A second bolus is then injected thorough the injection port 60 and a second downstream signal is generated as the second bolus passes the dilution sensor 40 downstream of the filter. Preferably, the second downstream signal is the mean transit time MTT1 for passage of the second bolus past the dilution sensor 40.

Thus, a change in FBV during operation of the filter 20 can be determined by introducing a first bolus upstream of the filter during operations of the filter; obtaining a signal downstream the filter corresponding to the passage of the first bolus through the filter and past the sensor 40; introducing a second bolus upstream of the filter during operation of the filter; obtaining a signal downstream the filter corresponding to the passage of the second bolus through the filter and past the sensor; and calculating the change in FBV from the signal obtained from the first and second bolus introduction.

It is understood the accuracy may be enhanced by determining a blood flow rate through the filter 20 and particularly a blood flow rate upstream and downstream of the filter. Thus, a change in the FBV can be determined in real time.

Figure 9:
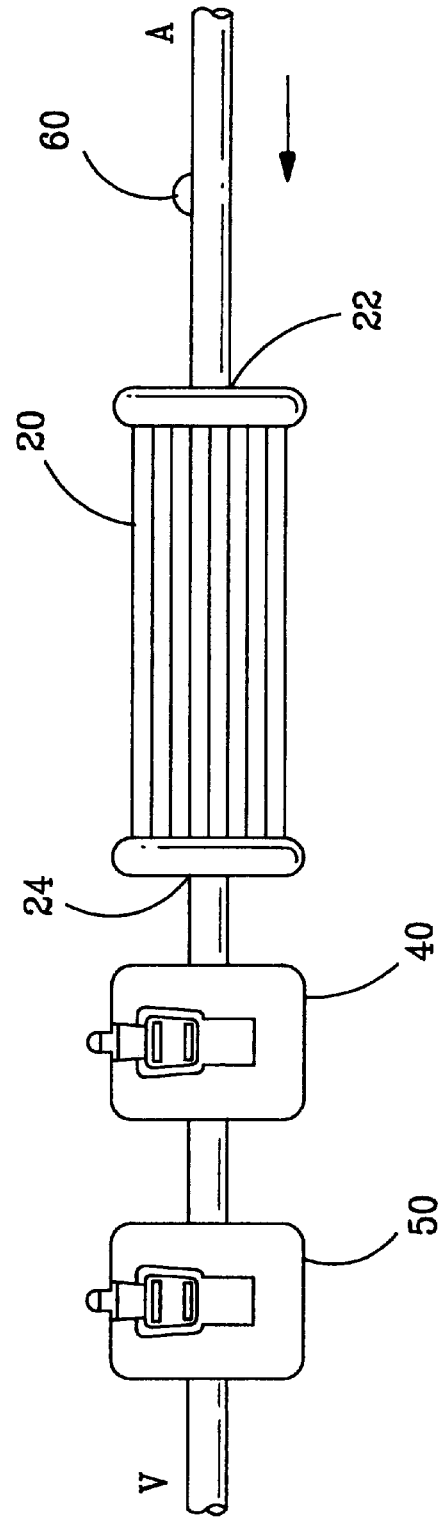
FIG. 9 is a schematic view of a portion of the system showing an apparatus for monitoring filter blood volume during operation of the filter.

Referring to FIG. 9, a configuration for monitoring a volume of blood in a blood filter 20 during operation of the filter is shown. This configuration includes a dilution sensor 40 on the blood side downstream of the filter and the injection port 60 on the blood side located upstream of the filter. In addition, the system includes a sensor 50 for measuring the blood side flow rate. Preferably, the sensor 50 is a flow rate sensor and is located downstream of the filter. It is also understood the flow rate may measured via the dilution sensor 40, thereby obviating the need for a separate flow rate sensor. In this system, the method determines FBV by the relationship:

$$V_B = Q_B(\text{MTTv})$$

where MTTv is the mean transit time of the bolus past the downstream (venous) dilution sensor and $Q_B$ is the flow rate through the blood filter.

In operation, a bolus is injected through the injection port 60 upstream of the filter 20. In a preferred condition, the bolus is introduced sufficiently near the filter 20 to substantially preclude compensation of a downstream signal. The flow rate is determined by the flow rate sensor 50, or via the dilution sensor 40, where the flow rate is calculated from the same dilution signal from the sensor 40. A signal corresponding to passage of the bolus past the dilution sensor 40 is obtained. Preferably, the signal is the mean transit time for passage of the bolus past the dilution sensor.

Thus, the FBV may be calculated by introducing a bolus upstream of the filter 20 during operation of the filter and sufficiently near the filter to substantially preclude compensation of a downstream signal; obtaining the downstream signal corresponding to passage of the bolus downstream of the filter; measuring a blood flow rate through the filter; and calculating the blood volume of the filter in response to the downstream signal and the measured blood flow rate.

Figure 10:
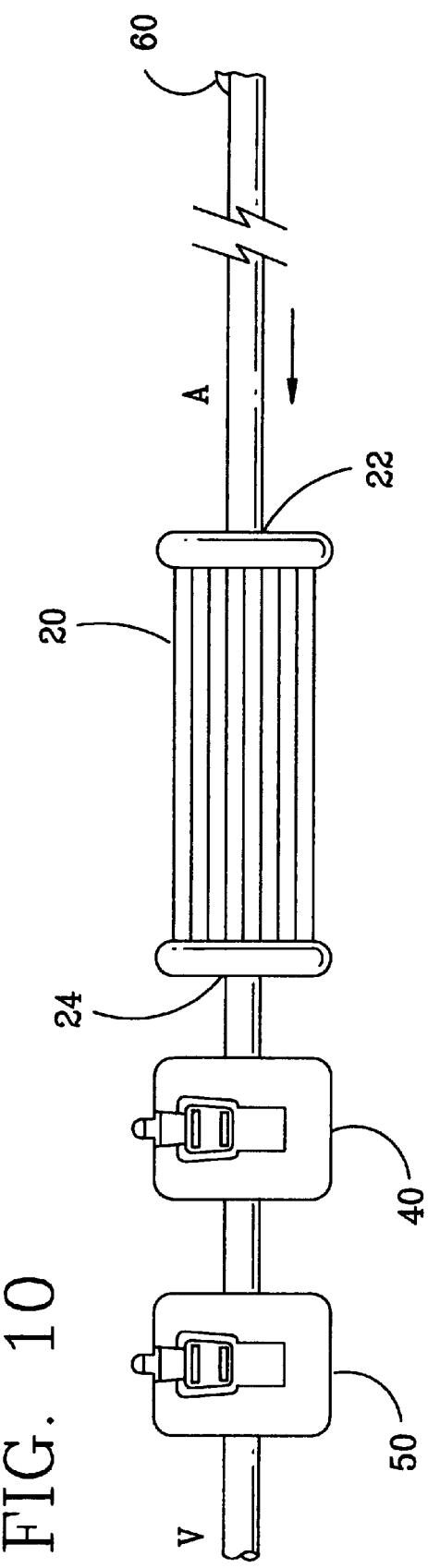
FIG. 10 is a schematic view of a portion of the system showing an alternative apparatus for monitoring filter blood volume in a filter during operation of the filter.

Referring to FIG. 10, a configuration for monitoring a volume of blood in a filter 20 during operation of the filter is shown. This configuration includes a blood side dilution sensor 40 downstream of the filter and an injection port 60 located on the blood side upstream of the filter. The injection port 60 is located sufficiently far upstream of the filter 20 that an accommodation or correction must be made for the volume of the tubing between the injection port and the filter. In addition, the system includes a sensor 50 for measuring the blood side flow rate. Preferably, the sensor 50 is a flow rate sensor is located downstream of the filter. It is also understood the flow rate may measured via the dilution sensor 40, thereby obviating the need for a separate flow rate sensor. In this system, the method determines FBV by the relationship:

$$V_B = Q_B\left(MTTv - \frac{V_{art}}{Q_B}\right)$$

where MTTv is the mean transit time of the bolus past the downstream (venous) dilution sensor and $V_{art}$ is the volume of the arterial section intermediate the injection port and the filter.

Thus, the FBV may be measured during operation of the filter 20 by introducing a bolus upstream of the filter during operation of the filter at a given time. A volume of blood intermediate the injection port 60 and the filter 20 is either determined, calculated or know (based upon tubing geometry). A signal is obtained downstream of the filter corresponding to the passage of the bolus. The signal may be the mean transit time. The blood flow rate through the filter 20 is measured by a flow rate sensor 50 or calculated from the dilution sensor 40. The FBV is then calculated based upon the given time, the signal obtained downstream the filter, the measured blood flow rate and the identified volume of blood between the place of in indicator introduction and the filter.

Figure 11:
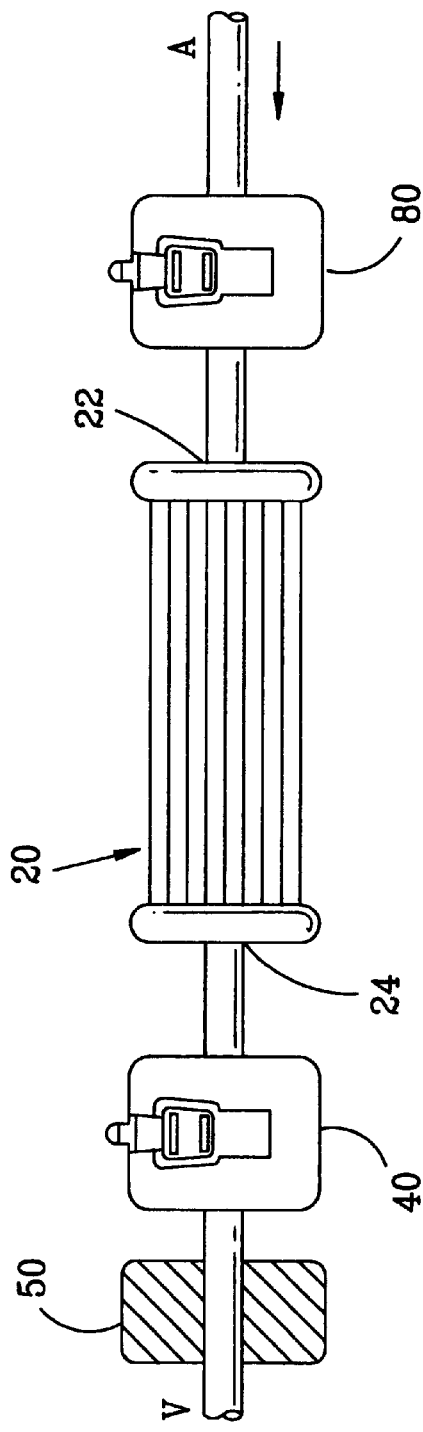
FIG. 11 is a schematic view of a portion of the system showing a further apparatus for monitoring filter blood volume in a blood filter during operation of the filter.

Referring to FIG. 11, a configuration for monitoring a volume of blood in a filter 20 during operation of the filter is shown. This configuration includes a blood side dilution sensor 80 upstream of the filter 20, a blood side dilution sensor 40 downstream of the filter and the injection port 60 located on the blood side and upstream of the filter. In addition, the system includes a sensor 50 for measuring the blood side flow rate. Preferably, the sensor 50 is a flow rate sensor is located downstream of the filter. It is also understood the flow rate may measured via the dilution sensor 40 or sensor 80, thereby obviating the need for a separate flow rate sensor. In this system, the method determines FBV by the relationship:

$$V_B = Q_B(MTTv - MTT_A)$$

where $MTT_A$ is the mean transit time of the bolus past the upstream (arterial) dilution sensor; MTTv is the mean transit time of the bolus past the downstream (venous) dilution sensor and $Q_B$ is the flow rate through the blood filter.

Thus, the configuration provides for measuring the FBV during operation of the filter 20 by first introducing a bolus upstream of the filter. An upstream signal is obtained corresponding to passage of the bolus past the upstream dilution sensor 80. A downstream signal is obtained corresponding to passage of the bolus past the downstream dilution sensor 40. The blood flow rate through the filter 20 is then measured, calculated or determined. Finally, the FBV is calculated in response to the upstream and downstream signals and the measured blood flow rate. It is understood the upstream signal and the downstream signal may correspond to the respective mean transit times. Further, the blood flow rate may be calculated from one of the upstream and the downstream dilution signals.

Figure 12:
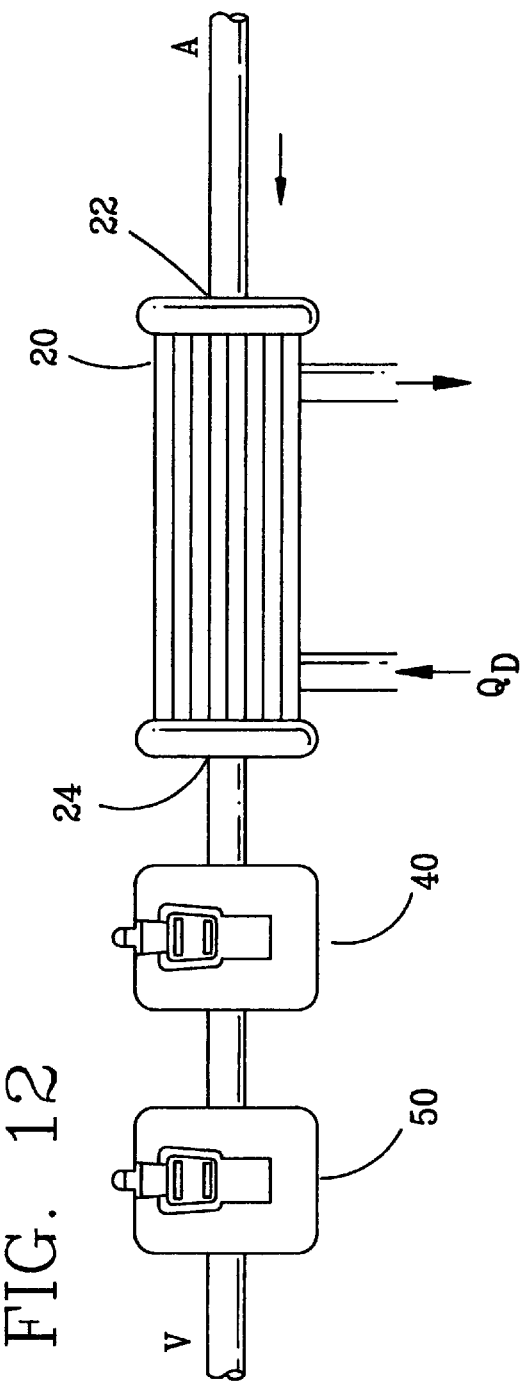
FIG. 12 is a schematic view of a portion of the system showing a further apparatus for monitoring filter blood volume in a blood filter during operation of the filter.

Referring to FIG. 12, a configuration for monitoring a volume of blood in a filter 20 during operation of the filter is shown. This configuration includes a dilution sensor 40 on the blood side downstream of the filter. In addition, the system includes a sensor 50 for measuring the blood side flow rate. Preferably, the sensor 50 is a flow rate sensor is located downstream of the filter. It is also understood the flow rate may measured via the dilution sensor 40, thereby obviating the need for a separate flow rate sensor. In this system, the method determines FBV by the relationship described in the previous section of the disclosure. This method employs a manipulation of the filtration rate and the corresponding time for the change in the blood property Thus, the FBV may be monitored during operation of the filter 20 by measuring a blood parameter downstream of the blood side of the filter. The blood flow rate through the blood side of the filter 20 is then measured, calculated or determined. The filtration rate is then changed to cause a change in the measured blood parameter. The FBV is then calculated corresponding to the measured change of the blood parameter and the blood flow rate.

Figure 13:
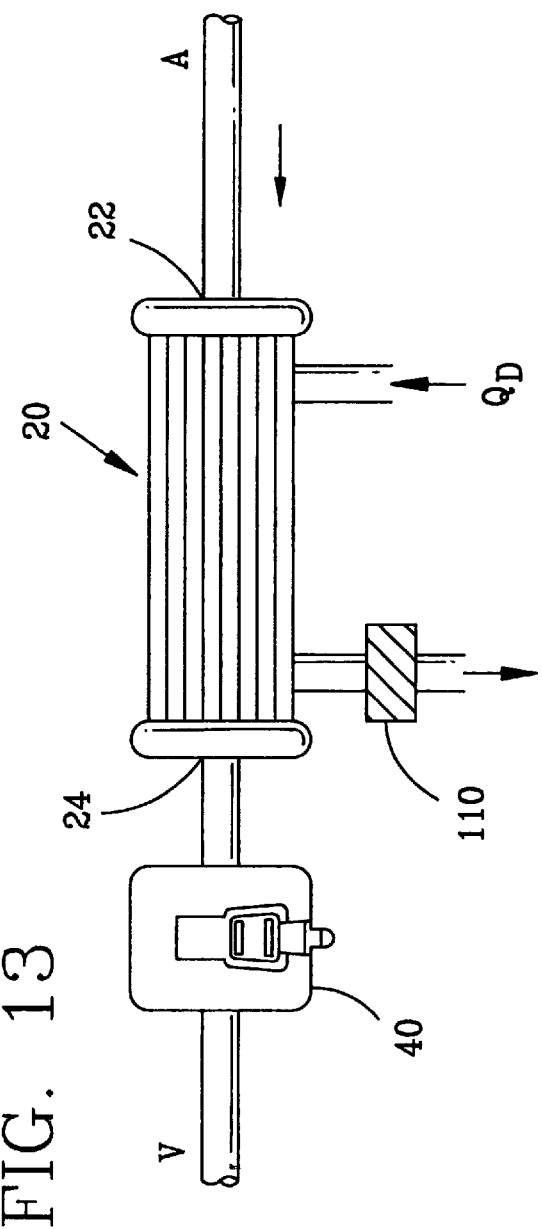
FIG. 13 is a schematic view of a portion of the system showing a further apparatus for monitoring filter blood volume in a blood filter during operation of the filter, the blood filter having a blood side and a dialysate side.

Referring to FIG. 13, a configuration for monitoring a volume of blood in a filter 20 during operation of the filter is shown. This configuration includes a blood side dilution sensor 40 downstream of the filter. In addition, the system includes a sensor 110 for measuring the dialysate flow rate. Preferably, the sensor 110 is a flow rate sensor and is located on the dialysate side of the filter 20 and downstream of the filter. In this system, the method determines FBV by the relationship described in the previous section of the disclosure.

Thus, the FBV may be monitored during operation of the filter 20 by measuring a blood parameter in the blood side downstream of the filter. The flow rate through the dialysate side of the filter is measured. The filtration rate of the filter 20 is changed to change the measured blood parameter. The FBV may then be calculated from the changed blood parameter and the measured flow rate through the dialysate side.

Referring to FIG. 14, a configuration for monitoring a volume of blood in a filter 20 during operation of the filter is shown. This configuration includes a dilution sensor 140 on the dialysate side of the filter, downstream of the filter. In addition, the system includes a sensor 110 for measuring the dialysate flow rate. Preferably, the sensor 110 is a flow rate sensor is located on the dialysate side of the filter 20 and upstream of the filter. An injection port 62 is provided on the dialysate side of the filter 20. In this system, the method determines FBV by the relationship:

$$V_B = Q_D(MTT_{diff} - V_{dialyzer})$$

where $Q_D$ is the flow rate through the dialysate side of the filter; $MTT_{diff}$ is the mean transit time for a diffusable bolus and $V_{dialyzer}$ is the volume of the dialysate side of the filter 20. The volume of the dialysate side of the filter 20 is generally known or may be readily calculated by traditional methods.

Thus, a volume of blood in a blood filter 20 may be measured during operation of the filter by changing a parameter of dialysate in the dialysate side of the filter upstream of the filter. Preferably, a diffusable bolus is passed through the filter 20 to change the blood parameter. A change in the dialysate downstream of the filter due to passing the diffusable bolus through the filter is measured. The blood flow rate in the dialysate side of the filter 20 is measured. Finally, FBV is calculated in response to the measured changes in dialysate parameter, the flow rate and the known volume of the dialysate side.

Referring to FIG. 15, a configuration for monitoring a volume of blood in a filter 20 during operation of the filter is shown. This configuration includes a dilution sensor 140 on the dialysate side of the filter, downstream of the filter. At least one injection port 62 and preferably two injection ports are located on the dialysate side of the filter 20. This configuration employs a first diffusable bolus and a second non diffusable bolus passing through the dialysate side of the filter 20. In this system, the method determines FBV by the relationship as set forth for FIG. 14 as well as that a second bolus is introduced:

$$V_{dialyzer} = Q_D MTT_{nondiff})$$

where $Q_D$ is the flow rate through the dialysate side of the filter; $MTT_{nondiff}$ is the mean transit time for the non diffusable bolus and $V_{dialyzer}$ is the volume of the dialysate side of the filter measured by dilution with the non diffusable bolus.

Hence, the blood volume of the filter 20 may be represented as $$FBV = Q_D(MTT_{diff} - MTT_{nondiff})$$

where $Q_D$ is the flow rate through the dialysate side of the filter; $MTT_{nondiff}$ is the mean transit time for the non diffusable bolus and $MTT_{diff}$ is the mean transit time for the diffusable bolus.

Thus, the FBV may be measured during operation of the filter 20 by injecting a non diffusable bolus upstream of the dialysate side of the filter. An injection or introduction of a diffusable bolus upstream of the dialysate side of the filter 20 is also made. A dilution curve corresponding to passage of the non diffusable bolus downstream of the filter 20 is measured. A dilution curve corresponding to passage of the diffusable bolus downstream of the filter 20 is also measured. The flow rate through the dialysate side of the filter is measured. Finally, the FBV is calculated in response to the dilution curve from diffusable bolus and nondiffusable bolus and the measured flow rate through the dialysate side.

Figure 16:
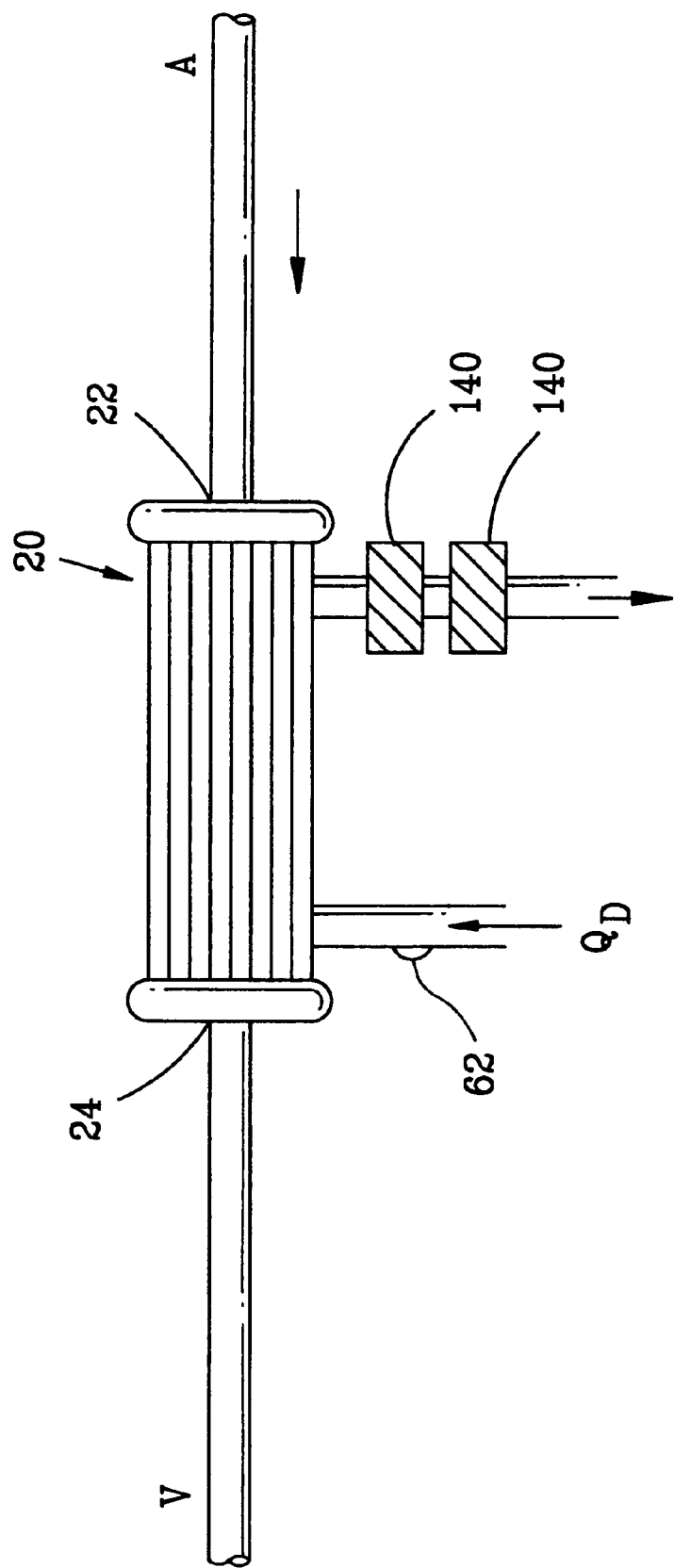
FIG. 16 is a schematic view of a portion of the system showing a further apparatus for monitoring filter blood volume in a blood filter during operation of the filter, the blood filter having a blood side and a dialysate side.
Figure 17:
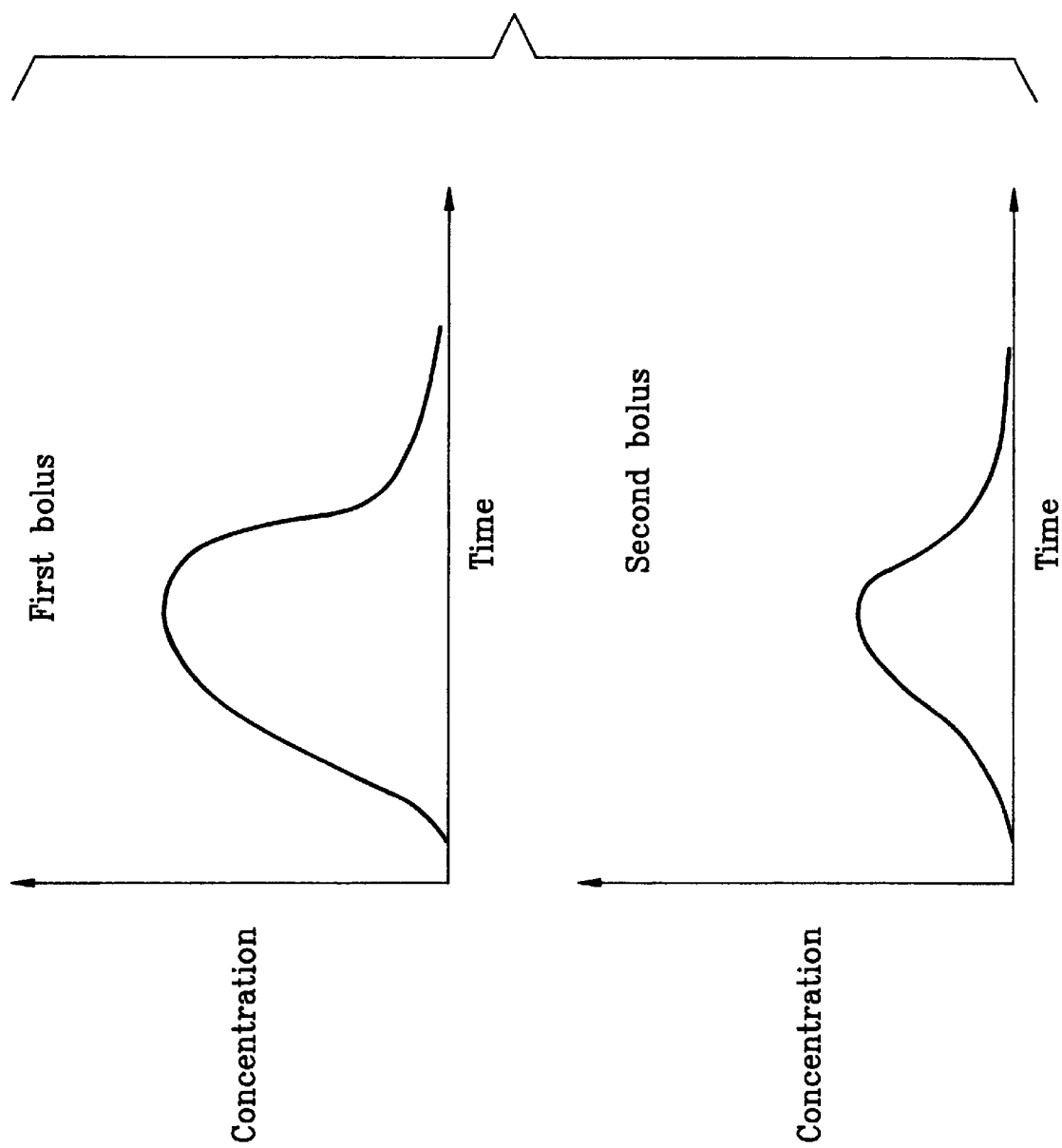
FIG. 17 is a pair of graphs showing the relationship of concentration of the blood versus time during passage of a first bolus and a second bolus.

Referring to FIG. 16, a configuration for monitoring a volume of blood in a filter during operation of the filter is shown. This configuration includes a first dilution sensor 140 and a second dilution sensor 140 on the dialysate side of the filter 20, downstream of the filter. This configuration employs a first diffusable bolus and a second non diffusable bolus passing through the dialysate side of the filter 20, wherein the first bolus and the second bolus are substantially simultaneously introduced.

Thus, a volume of blood in a blood filter 20 may be measured during operation of the filter by injecting a bolus of a diffusable indicator and a non diffusable indicator upstream of the filter on the dialysate side of the filter. A dilution curve corresponding to passage of the diffusable indicator downstream of the filter on dialysate side is measured by the first dilution sensor 140. A dilution curve corresponding to passage of the non diffusable indicator downstream of the filter on dialysate side is measured by the second dilution sensor 140. The flow rate through the dialysate side is measured. Finally, a FBV is calculated from dilution curves of the diffusable indicator and the nondiffusable indicator and the measured flow rate through the dialysate side of the filter.

As previously stated, the present invention may include a feedback system for selectively triggering an alarm, upon a predetermined change in the measured volume of the filter, or a heparin infusion or other anticoagulant or other treatment substance. Alternatively, the alarm may be triggered by a change in the volume, independent of the measured volume. The feedback may be configured as a loop or a single direction signal which prompts operator response.

Figure 18:
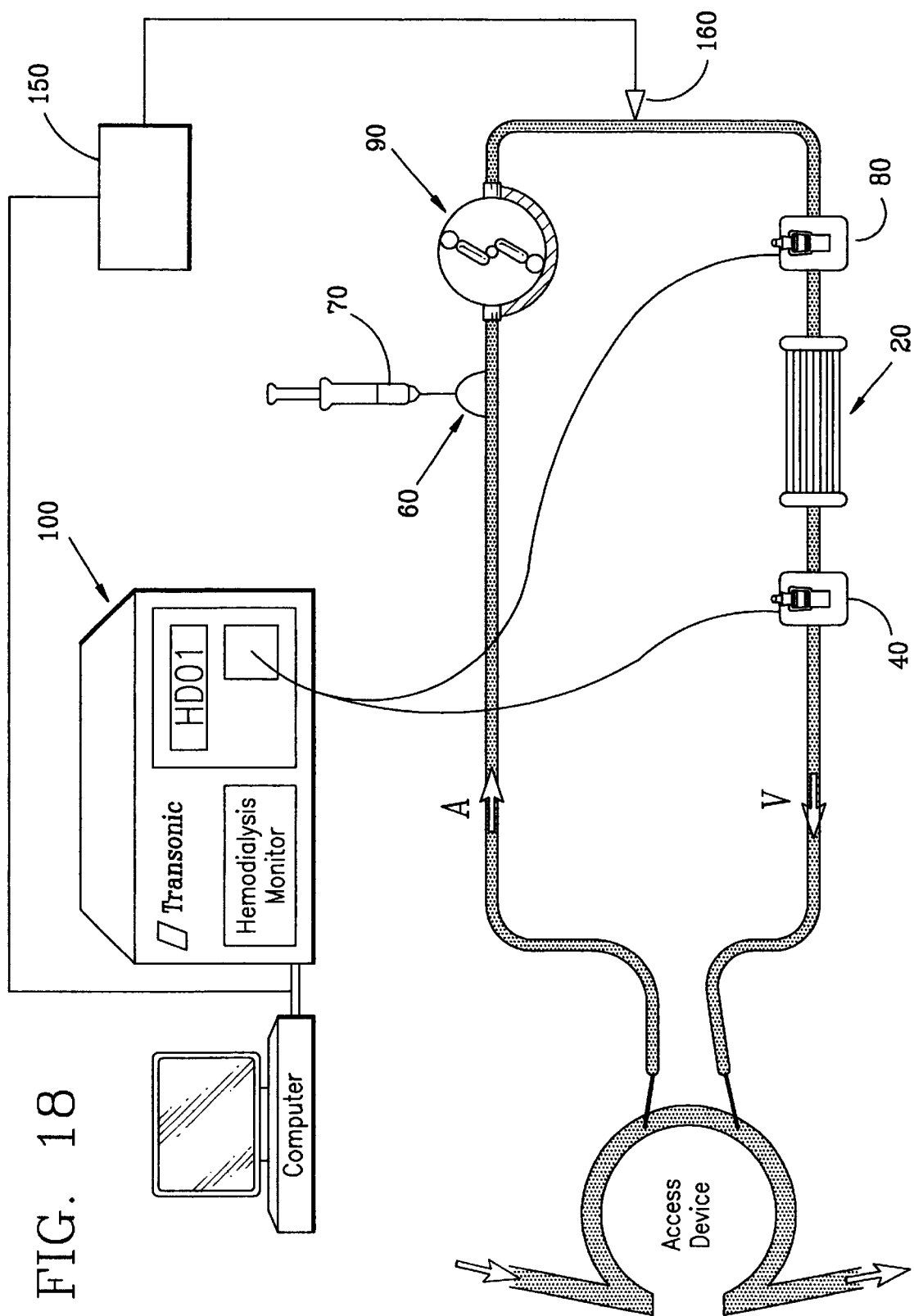
FIG. 18 is a system view of a filter incorporated in a circulation system having an apparauts for measuring filter blood volume and an alarm system operably connected to the measuring apparatus.

Referring to FIG. 18, each of the configurations of the present invention may be employed in cooperation with an alarm (alert) system 150 and/or a blood characteristic modifier 160 such as an infusion system.

The alarm system 150 is operably connected to the evaluating device 100 and may provide an alarm in response to a signal from the evaluating device. The alarm signal may be set to respond to a predetermined change in FBV volume, an absolute FBV or a combination of both. The alarm may be in the form of an audible alarm or a visual alarm. In addition, it is contemplated the alarm system 150 is operably connected to the blood characteristic modifier 160. Thus, in addition to, or in place of the alarm, the blood characteristic modifier 160 may automatically alter a parameter of the system by changing filtration rates, discontinuing a process or adding material to the blood flow, such as through an infusion device.

The blood characteristic modifier 160 may be operably located at any point in the circulation system as dictated by the intended operation and type of modification. For example, the blood characteristic modifier 160 may be connected to the blood flow path, the filter 20 or a fluid system in conjunction with the filter. The present invention thereby provides a method and apparatus for monitoring the FBV (or change in FBV) and a feedback and control system for responding, either selectively or automatically, to the monitored FBV.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims which scope is to be accorded the broadest interpretation so as to encompass all such modifications and equivalent structures.

What is claimed is:

1. A method for monitoring a volume of blood in a blood filter, the method comprising:
   (a) measuring a blood parameter downstream of a blood side of the filter;
   (b) determining a blood flow rate through the blood side of the filter;
   (c) changing a filtration rate of the filter to change the blood parameter;
   (d) measuring a resulting change of the blood parameter downstream of the blood side of the filter; and
   (e) calculating the blood volume from the resulting change of the blood parameter and the blood flow rate.

2. A method for monitoring a blood volume of a blood filter, the blood filter having a blood side and a dialysate side, the method comprising:
   (a) measuring a blood parameter in the blood side downstream of the filter;
   (b) determining a flow rate through the dialysate side;
   (c) changing a filtration rate to change the blood parameter; and
   (d) measuring a resulting change in the blood parameter from the changing filtration rate.

3. The method of claim 2, further comprising calculating a filter blood volume corresponding to the determined flow rate and the measured resulting change in the blood parameter.

4. A method for monitoring a blood volume in a blood filter, the blood filter having a blood side and a dialysate side having a known volume, the method comprising:
   (a) changing a parameter of dialysate in the dialysate side upstream of the filter by passing a diffusable bolus through the filter;
   (b) measuring a change of dialysate downstream the filter due to passing the diffusable bolus through the filter; and
   (c) determining a flow rate in the dialysate side.

5. The method of claim 4, further comprising calculating a blood volume in the blood side corresponding to the measured changes in dialysate parameter, the flow rate and the known volume of the dialysate side.

6. A method for monitoring a change in a volume of blood in a filter, comprising:
   (a) obtaining a first blood parameter measurement downstream of a blood side of the filter, the first blood parameter corresponding to a first filtration rate change; and
   (b) obtaining a second blood parameter measurement downstream of a blood side of the filter, the second blood parameter corresponding to a second filtration rate change.

7. The method of claim 6, further comprising calculating a change in the volume of blood in the filter from the first blood parameter measurement and the second blood parameter measurement.

* * * * *

UNITED STATES PATENT AND TRADEMARK OFFICE
CERTIFICATE OF CORRECTION

PATENT NO. : 6,548,017 B2  Page 1 of 1
DATED : April 15, 2003
INVENTOR(S) : Krivitski, Nikolai M. and Kislukhin, Victor V.

It is certified that error appears in the above-identified patent and that said Letters Patent is hereby corrected as shown below:

<u>Title page, Item [63] and Column 1, line 6,</u>
Reading "5,928,128", should read -- 5,928,180 --.

Signed and Sealed this

Sixteenth Day of September, 2003

JAMES E. ROGAN
*Director of the United States Patent and Trademark Office*